United States Patent
Bongiorni et al.

(10) Patent No.: US 10,683,528 B2
(45) Date of Patent: Jun. 16, 2020

(54) ENHANCED PROTEIN EXPRESSION

(71) Applicant: DANISCO US INC., Palo Alto, CA (US)

(72) Inventors: Cristina Bongiorni, Fremont, CA (US); Rodante Gonzales Caguiat, Santa Clara, CA (US); Carol Marie Fioresi, Redwood City, CA (US); Brian F. Schmidt, Half Moon Bay, CA (US); Anita Van Kimmenade, Woodside, CA (US); Chao Zhu, Mountain View, CA (US)

(73) Assignee: DANISCO US INC, Palo Alto, CA (US)

( * ) Notice: Subject to any disclaimer, the term of this patent is extended or adjusted under 35 U.S.C. 154(b) by 0 days.

(21) Appl. No.: 15/529,948

(22) PCT Filed: Dec. 3, 2015

(86) PCT No.: PCT/US2015/063636
§ 371 (c)(1),
(2) Date: May 25, 2017

(87) PCT Pub. No.: WO2016/099917
PCT Pub. Date: Jun. 23, 2016

(65) Prior Publication Data
US 2017/0362628 A1    Dec. 21, 2017

Related U.S. Application Data

(60) Provisional application No. 62/092,461, filed on Dec. 16, 2014.

(51) Int. Cl.
| | | |
|---|---|---|
| *C12P 21/02* | (2006.01) | |
| *C07K 14/32* | (2006.01) | |
| *A61K 35/74* | (2015.01) | |
| *C12N 1/20* | (2006.01) | |
| *C12N 9/28* | (2006.01) | |
| *C12N 9/54* | (2006.01) | |
| *C12N 9/88* | (2006.01) | |
| *C12N 15/75* | (2006.01) | |

(52) U.S. Cl.
CPC .............. *C12P 21/02* (2013.01); *C07K 14/32* (2013.01); *C12N 9/2417* (2013.01); *C12N 9/54* (2013.01); *C12N 9/88* (2013.01); *C12N 15/75* (2013.01); *C12Y 302/01001* (2013.01); *C12Y 304/21062* (2013.01); *C12Y 402/02002* (2013.01)

(58) Field of Classification Search
None
See application file for complete search history.

(56) References Cited

U.S. PATENT DOCUMENTS

| | | |
|---|---|---|
| 4,302,544 A | 11/1981 | Young et al. |
| 4,450,235 A | 5/1984 | Dean et al. |
| 4,683,195 A | 7/1987 | Mullis et al. |
| 4,683,202 A | 7/1987 | Mullis |
| 4,760,025 A | 7/1988 | Estell et al. |
| 4,914,031 A | 4/1990 | Zukowski et al. |
| 4,965,188 A | 10/1990 | Mullis et al. |
| 4,980,288 A | 12/1990 | Bryan et al. |
| 5,208,158 A | 5/1993 | Bech et al. |
| 5,217,878 A | 6/1993 | Van et al. |
| 5,264,366 A | 11/1993 | Ferrari et al. |
| RE34,606 E | 5/1994 | Estell |
| 5,310,675 A | 5/1994 | Estell et al. |
| 5,322,770 A | 6/1994 | Gelfand |
| 5,336,611 A | 8/1994 | Van et al. |
| 5,399,283 A | 3/1995 | Stabinsky et al. |
| 5,441,882 A | 8/1995 | Estell et al. |
| 5,482,849 A | 1/1996 | Branner et al. |
| 5,631,217 A | 5/1997 | Branner et al. |
| 5,665,587 A | 9/1997 | Aaslyng et al. |
| 5,700,676 A | 12/1997 | Bott et al. |
| 5,741,694 A | 4/1998 | Hastrup et al. |
| 5,858,757 A | 1/1999 | Von et al. |
| 5,880,080 A | 3/1999 | Amory et al. |
| 6,197,567 B1 | 3/2001 | Aaslyng et al. |
| 6,218,165 B1 | 4/2001 | Estell et al. |
| 2014/0314716 A1* | 10/2014 | Pomerantsev .......... C12P 21/02 424/93.2 |

FOREIGN PATENT DOCUMENTS

| | | |
|---|---|---|
| EP | 0134048 A1 | 3/1985 |
| EP | 0414279 B1 | 11/1993 |
| WO | 89/06279 A1 | 7/1989 |

(Continued)

OTHER PUBLICATIONS

Chai et al. A Widely Conserved Gene Cluster Required for Lactate Utilization in Bacillus subtilis and its Involvement in Biofilm Formation. Apr. 2009. Journal of Bacteriology. vol. 191, No. 8, pp. 2432-2430. (Year: 2009).*

(Continued)

*Primary Examiner* — Channing S Mahatan

(57) ABSTRACT

The present invention relates in general to bacterial cells having genetic alterations that result in increased expression of a protein of interest and methods of making and using such cells. Aspects of the present invention include altered Gram positive microorganisms having one or more a genetic alterations that reduce the expression of a gene in the sin operon, thereby resulting in the enhanced expression of one or more proteins of interest.

13 Claims, 8 Drawing Sheets

Specification includes a Sequence Listing.

(56) References Cited

FOREIGN PATENT DOCUMENTS

| WO | 99/20726 A1 | 4/1999 |
| WO | 99/20769 A2 | 4/1999 |
| WO | 99/20770 A2 | 4/1999 |
| WO | 03/83125 A1 | 10/2003 |
| WO | 2010/144283 A1 | 12/2010 |

OTHER PUBLICATIONS

Leiman et al. SinR is a mutational target for fine-tuning biofilm formation in laboratory-evolved strains of Bacillus subtilis. Published online Nov. 30, 2014. BMC Microbiol. vol. 14, No. 301, 10 pages. (Year: 2014).*

Altschul et al., "Local Alignment Statistics," Meth. Enzymol., 1993, vol. 266, pp. 460-480.

Altschul et al., "Basic Local Alignment Search Tool," J. Mol. Biol., 1990, vol. 215, pp. 403-410.

Zukowski, "Production of commercially valuable products," In Biology of Bacilli: Applications to Industry, 1992, Doi and McGlouglin (eds.), Butterworth-Heinemann, Stoneham, Mass, pp. 311-337.

Wu et al., "The Ligation Amplification Reaction (LAR)-Amplification of Specific DNA Sequences Using Sequential Rounds of Template-Dependent Ligation," Genomics, 1989, vol. 4, pp. 560-569.

Wells et al., "Cloning, sequencing, and secretion of Bacillus amyloliquefaciens subtilisin in Bacillus subtilis," Nucleic Acids Res., 1983, vol. 11, pp. 7911-7925.

Ward, "Proteinases," In Microbial Enzymes and Biotechnology, Fogarty (ed.)., Applied Science, London, 1983, pp. 251-317.

Wang et al., "Expression and secretion of human atrial natriuretic a-factor in Bacillus subtilis using the signel peptide," Gene, 1988, vol. 69, pp. 39-47.

Vorobjeva et al., "Transformation of Bacillus Megaterium Protoplasts by Plasmid DNA," FEMS Microbiol. Lett., 1980, vol. 7, pp. 261-263.

Voigt, et al., "The Bacillus subtilis sin Operon: An Evolvable Network Motif," Genetics, 2004, vol. 169, No. 3, pp. 1187-1202.

Vasantha et al., "Genes for Alkaline Protease and Neutral Protease from Bacillus amyloliquefaciens Contain a Large Open Reading Frame Between the Regions Coding for Signal Sequence and Mature Protein," J. Bacteriol., 1984, vol. 159, No. 3, pp. 811-819.

Thompson et al., "CLUSTAL W: improving the sensitivity of progressive multiple sequence alignment through sequence weighting, position-specific gap penalties and weight matrix choice," Nucleic Acids Res., 1994, vol. 22, pp. 4673-4680.

Stahl et al., "Replacement of the Bacillus subtilis Subtilisin Structural Gene with an In Vitro-Derived Deletion Mutation," J. Bacteriol., 1984, vol. 158, pp. 411-418.

Smith et al., "Protoplast Transformation in Coryneform Bacteria and Introduction of an a-Amylase Gene from Bacillus amyloliquefaciens into Brevibacterium lactofermentum," Appl. Env. Microbiol., 1986, vol. 51, pp. 634-639.

Smith et al., "Comparison of Biosequences," Adv. Appl. Math., 1981, vol. 2, pp. 482-489.

Saunders et al., "Use of Chromosomal Integration in the Establishment and Expression of blaZ, a *Staphylococcus aureus* β-Lactamase Gene, in Bacillus subtilis," J. Bacteriol., 1984, vol. 157, pp. 718-726.

Priest, "Extracellular Enzyme Synthesis in the Genus *Bacillus*," Bacterial. Rev., 1977, vol. 41, pp. 711-753.

Perego, "Integrational Vectors for Genetic Manipulation in Bacillus subtilis," In Bacillus subtilis and Other Gram-Positive Bacteria, 1993, Sonenshein et al. (eds.), American Society for Microbiology, Washington, DC, pp. 615-624.

Perego et al., "The oligopeptide transport system of Bacillus subtilis plays a role in the initiation of sporulation," Mol. Microbiol., 1991, vol. 5, pp. 173-185.

Pearson et al., "Improved tools for biological sequence comparison," Proc. Natl. Acad. Sci. USA, 1988, vol. 85, pp. 2444-2448.

PCT International Search Report and the Written Opinion of the International Searching Authority for International Application No. PCT/US2015/063636; ISA/EPO; dated Apr. 28, 2016.

Palva et al., "Molecular cloning of a-amylase gene from BacHlus amyloliquelaciens and its expression in B. subtilis," Gene, 1982, vol. 19, pp. 81-87.

Palmeros et al., "A family of removable cassettes designed to obtain antibiotic-resistance-free genomic modifications of *Escherichia coli* and other bacteria," Gene, 2000, vol. 247, pp. 255-264.

Olmos et al., "Effects of the sinR and degU32 (Hy) mutations on the regulation of the aprE gene in Bacillus subtilis," Mol. Gen. Genet., 1997, vol. 253, pp. 562-567.

Needleman et al., "A General Method Applicable to the Search for Similarities in the Amino Acid Sequence of Two Proteins," J. Mol. Biol., 1970, vol. 48, pp. 443-453.

Msadek et al., "Signal Transduction Pathway Controlling Synthesis of a Class of Degradative Enzymes in Bacill's subtilis: Expression of the Regulatory Genes and Analysis of Mutations in degS and degU," J. Bacteriol., 1990, vol. 172, pp. 824-834.

Morinaga et al., "Improvement of Oligonucleotide-Directed Site-Specific Mutagenesis Using Doublestranded Plasmid DNA," Bio/Technology, 1984, vol. 2, pp. 636-639.

McDonald et al., "Plasmid Transformation of Bacillus sphaericus 1593," J. Gen. Microbiol., 1983, vol. 130, pp. 203-208.

Mann et al., "Transformation of *Bacillus* spp.: an Examination of the Transformation of Bacillus Pro top lasts by Plasmids p UB 110 and pHV33," Current Microbiol., 1986, vol. 13, pp. 131-135.

Maddox et al., "Elevated Serum Levels in Human Pregnancy of a Molecule Immunochemically Similar to Eosinophil Granule Major Basic Protein," J. Exp. Med., 1983, vol. 158, pp. 1211-1225.

Kuroda et al., "High-level transcription of the major Bacillus subtilis autolysin operon depends on expression of the sigma D gene and is affected by a sin (flaD) mutation," Journal of Bacteriology, 1993 vol. 175, No. 3, pp. 795-801.

Kuhn et al., "Cre/loxP Recombination System and Gene Targeting," Meth. Mol. Biol., 2002, vol. 180, pp. 175-204.

Kramer et al., "The gapped duplex DNA approach to oligonnucleotide-directed mutation construction," Nucleic Acids Res., 1984, vol. 12, pp. 9441-9456.

Klier et al., "Positive Regulation in the Gram-Positive Bacterium: *Bacillus subtilus*," Annual Review of Microbiology, 1992, vol. 46, pp. 429-459.

Karlin et al., "Applications and statistics for multiple high-scoring segments in molecular sequences," Proc. Natl. Acad. Sci. USA, 1993, vol. 90, pp. 5873-5787.

Kacian et al., "A Replicating RNA Molecule Suitable for a Detailed Analysis of Extracellular Evolution and Replication," Proc. Natl. Acad. Sci. USA, 1972, vol. 69, pp. 3038-3042.

Hsia et al., "Active-Site Titration of Serine Proteases Using a Fluoride Ion Selective Electrode and Sulfonyl Fluoride Inhibitors," Anal Biochem., 1996, vol. 242, pp. 221-227.

Holubova et al., "Transfer of Liposome-Eneapsulated Plasmid DNA to Bacillus subtilis Protoplasts and Calcium-Treated *Escherichia coli* Cells," Folia Microbiol., 1985, vol. 30, pp. 97-109.

Hoch et al., "Transformation and Transduction in Recombination-defective Mutants of Bacillus subtilis," J. Bacteriol., 1967, vol. 93, pp. 1925-1937.

Higgins et al., "Fast and sensitive multiple sequence alignments on a microcomputer," Cabios Communications, 1989, vol. 5, pp. 151-153.

Harunur et al., "flaD (sinR) Mutations Affect SigD-Dependent Functions at Multiple Points in Bacillus subtilis," Journal of Bacteriology, 1996, vol. 178, No. 22, pp. 6640-6643.

Gaur et al., "Characterization of a Cloned Bacillus subtilis Gene That Inhibits Sporulation in Multiple Copies," J. Bacteriol., 1986, vol. 168, pp. 860-869.

Fischer et al., "Introduction of plasmid pC194 into Bacillus thuringiensis by protoplast transformation and plasmid transfer," Arch. Microbiol., 1981, vol. 139, pp. 213-217.

Ferrari et al., "Genetics," In Bacillus, 1989, Hardwood et al, (eds.), Plenum Publishing Corp., pp. 57-72.

(56) References Cited

OTHER PUBLICATIONS

Feng et al., "Progressive Sequence Alignment as a Prerequisite to Correct Phylogenetic Trees," J. Mol. Evol., 1987, vol. 35, pp. 351-360.

Fahnestock et al., "Expression of the Staphylococcal Protein A Gene in Bacillus subtilis by Gene Fusions Utilizing the Promoter from a Bacillus amyloliquefaciens a-Amylase Gene," J. Bacteriol., 1986, vol. 165, pp. 796-804.

Devereux et al., "A comprehensive set of sequence analysis programs for the VAX," Nucl. Acid Res., 1984, vol. 12, pp. 387-395.

Dayhoff et al., "A Model of Evolutionary Change in Proteins," In Atlas of Protein Sequence and Structure, 1978, National Biomedical Research Foundation, Washington, D.C., vol. 5: Suppl. 3, pp. 345-352.

Christianson et al., "Peptide Mapping of Subtilisins as a Practical Tool for Locating Protein Sequence Errors during Extensive Protein Engineering Projects," Anal. Biochem., 1994, vol. 223, pp. 119-129.

Chang et al., "High Frequency Transformation of Bacillus subtilis Protoplasts by Plasmid DNA," Mol. Gen. Genet., 1979, vol. 168, pp. 111-115.

Chamberlin et al., "New RNA Polymerase from *Escherichia coli* infected with Bacteriophage T7," Nature, 1970, vol. 228, pp. 227-231.

Caldwell et al., "Correlation between Bacillus subtilis scoC Phenotype and Gene Expression Determined Using Microarrays for Transcriptome Analysis," J. Bacteriol., 2001, vol. 183, pp. 7329-7340.

Aunstrup et al., "Proteases From Alkalophilic *Bacillus* Species," Proc. IV IFS: Ferment. Technol. Today, 1972, pp. 299-305.

\* cited by examiner

ENHANCED PROTEIN EXPRESSION

CROSS-REFERENCE TO RELATED APPLICATIONS

The present application is the National Stage of International Application PCT Patent Application No. PCT/US2015/063636, filed on Dec. 3, 2015, which claims priority under 35 U.S.C. § 119 to U.S. Provisional Patent Application No. 62/092,461, filed Dec. 16, 2014, the entirety of which is hereby incorporated by reference.

FIELD OF THE INVENTION

The present invention is generally related to the fields of molecular biology, cell biology, microbiology, genetics and protein production. More particularly, in various embodiments disclosed herein, the invention is directed to Gram positive bacterial cells having genetic alterations that result in increased expression of a protein of interest and methods of making and using such cells.

REFERENCE TO SEQUENCE LISTING

The contents of the electronic submission of the text file Sequence Listing, which is named 20150525NB40772-US-PCT_SequenceListing, was created on Oct. 29, 2015 May 25, 2017 and is 11 KB in size, is incorporated herein by reference.

BACKGROUND OF THE INVENTION

Genetic engineering has allowed the improvement of microorganisms used as industrial bioreactors, cell factories and in food fermentations. Gram-positive organisms, including a number of *Bacillus* species, are used to produce a large number of useful proteins and metabolites (see, e.g., Zukowski, "Production of commercially valuable products," In: Doi and McGlouglin (eds.) *Biology of Bacilli: Applications to Industry*, Butterworth-Heinemann, Stoneham, Mass. pages 311-337, 1992). Common *Bacillus* species used in industry include *B. licheniformis, B. amyloliquefaciens* and *B. subtilis*. Because of their GRAS (generally recognized as safe) status, strains of these *Bacillus* species are natural candidates for the production of proteins utilized in the food and pharmaceutical industries. Examples of proteins produced in Gram-positive organisms include enzymes such as α-amylases, neutral proteases, alkaline (or serine) proteases and the like.

In spite of advances in the understanding of production of proteins in bacterial host cells, there remains a need in the art to develop new recombinant bacterial strains that express increased levels of a protein of interest.

SUMMARY OF THE INVENTION

Certain embodiments of the present invention are directed to recombinant Gram positive cells that express increased levels of a protein of interest and methods of making and using the same. In particular, certain embodiments are directed to bacterial cells having genetic alterations that result in increased expression of a protein of interest as compared to bacterial cells that do not have the genetic alteration.

Thus, certain emdodiments disclosed herein are directed to methods for increasing expression of a protein of interest (hereinafter, a "POI") in a Gram positive bacterial cell. More particularly, certain embodiments are directed to methods for increasing expression of a POI in a Gram positive bacterial cell comprising (a) obtaining an altered Gram positive bacterial cell producing a POI, wherein the altered Gram positive bacterial cell comprises at least one genetic alteration that reduces expression of one or more genes in the sin operon and (b) culturing the altered Gram positive bacterial cell under conditions such that the POI is expressed, wherein the amount of a POI is increased relative to the expression of the same POI in an unaltered Gram positive bacterial cell.

In other embodiments the invention is directed to compositions comprising altered Gram positive bacterial cells. In certain embodiments, the invention provides altered Gram positive bacterial cells expressing an increased amount of a POI, relative to the expression of the same POI in an unaltered Gram positive bacterial control cell, wherein the altered bacterial cell comprises at least one genetic alteration that reduces expression of one or more genes in the sin operon.

An altered Gram positive bacterial cell of the instant disclosure may be any member of the *Bacillus* genus. In certain embodiments, the *Bacillus* cell is selected from the group consisting of *B. subtilis, B. licheniformis, B. lentus, B. brevis, B. stearothermophilus, B. alkalophilus, B. amyloliquefaciens, B. clausii, B. sonorensis, B. halodurans, B. pumilus, B. lautus, B. pabuli, B. cereus, B. agaradhaerens, B akibai, B. clarkii, B. pseudofirmus, B. lehensis, B. megaterium, B. coagulans, B. circulans, B. gibsonii*, and *B. thuringiensis*. In certain other embodiments, the *Bacillus* cell is *B. subtilis* or *B. licheniformis*. In certain other embodiments, the *Bacillus* cell is *B. subtilis* or *B. licheniformis*.

In certain embodiments a POI is encoded by a gene exogenous to the altered bacterial cell or a gene endogenous to the altered bacterial cell. In certain embodiments, the POI is an enzyme. In other embodiments, the POI is an enzyme selected from the group consisting of acetyl esterases, aminopeptidases, amylases, arabinases, arabinofuranosidases, carboxypeptidases, catalases, cellulases, chitinases, chymosin, cutinase, deoxyribonucleases, epimerases, esterases, α-galactosidases, β-galactosidases, α-glucanases, glucan lysases, endo-β-glucanases, glucoamylases, glucose oxidases, α-glucosidases, β-glucosidases, glucuronidases, hemicellulases, hexose oxidases, hydrolases, invertases, isomerases, laccases, lipases, lyases, mannosidases, oxidases, oxidoreductases, pectate lyases, pectin acetyl esterases, pectin depolymerases, pectin methyl esterases, pectinolytic enzymes, perhydrolases, polyol oxidases, peroxidases, phenoloxidases, phytases, polygalacturonases, proteases, rhamno-galacturonases, ribonucleases, transferases, transport proteins, transglutaminases, xylanases, hexose oxidases, and combinations thereof.

In certain embodiments, the POI is a protease. In certain embodiments, the protease is a subtilisin. In certain other embodiments, the subtilisin is selected from the group consisting of subtilisin 168, subtilisin BPN', subtilisin Carlsberg, subtilisin DY, subtilisin 147, subtilisin 309, and variants thereof.

In other embodiments, such altered Gram positive bacterial cells and methods thereof further comprise recovering the POI. In particular embodiments the increased amount of an expressed POI relative to the unaltered Gram positive control cell is at least 10%.

In certain other embodiments, the altered Gram positive bacterial cell (and methods thereof) further comprises a mutation in a gene selected from the group consisting of degU, degQ, degS, scoC4, and oppA. In certain embodiments, the mutation is degU(Hy)32.

Certain other embodiments are directed to a polynucleotide variant derived from a wild-type sinR gene having at least 80% sequence identity to SEQ ID NO: 1, wherein the polynucleotide variant comprises a missense mutation, a frameshift mutation, a nonsense mutation, an insertion and/or a deletion. In certain embodiments, the polynucleotide variant comprises a silent mutation at nucleotide position corresponding to nucleotide 330 of SEQ ID NO: 1. In particular embodiments, the silent mutation is at position corresponding to nucleotide 330 of SEQ ID NO: 1, wherein the silent mutation is a G to A nucleotide substitution.

Certain other embodiments are directed vectors comprising one or more polynucleotide variants of the invetion. In other embodiments, a vector is a targeting vector which replaces the endogenous chromosomal sinR gene by homologous recombination.

Certain other embodiments are directed to methods for increasing the expression of a protein of intrest (POI) in a Gram positive bacterial cell comprising (a) transforming a parental Gram positive bacterial cell with a vector comprising a polynucleotide variant, wherein homologous recombination between the vector and the corresponding region of parental sinR gene produces an altered Gram positive bacterial cell, and (b) culturing the altered cell under conditions suitable for the expression of the POI, wherein the increased expression of the POI is relative to the expression of the same POI in an unaltered Gram positive bacterial cell.

In certain embodiments, the altered Gram positive bacterial cell expresses a protein of interest, wherein an expression cassette encoding the POI is introduced into the parental Gram positive bacterial cell.

In other embodiments, the methods (and compositions thereof) further comprise culturing the altered Gram positive bacterial cell under conditions such that the protein of interest is expressed by the altered Gram positive bacterial cell. In particular embodiments, the compositions and methods thereof further comprises recovering the POI.

In certain embodiments, at least one mutation is a silent mulation wherein the mutation is at a nucleotide position corresponding to nucleotide 729 of SEQ ID NO: 1. In certain embodiments, the mutation is a C to T mutation at a nucleotide position corresponding to nucleotide 729 of SEQ ID NO: 1. In certain embodiments, the polynucleotide variant sequence is at least 90% identical to all or a part of SEQ ID NO:3. In certain embodiments, the variant sequence is identical to all or a part of SEQ ID NO:3. In certain embodiments, the variant sequence is at least 20 nucleotides in length. In certain embodiments, the variant sequence is at least 50 nucleotides in length. In certain embodiments, the variant sequence is at least 200 nucleotides in length.

DETAILED DESCRIPTION OF THE INVENTION

Figure 1:
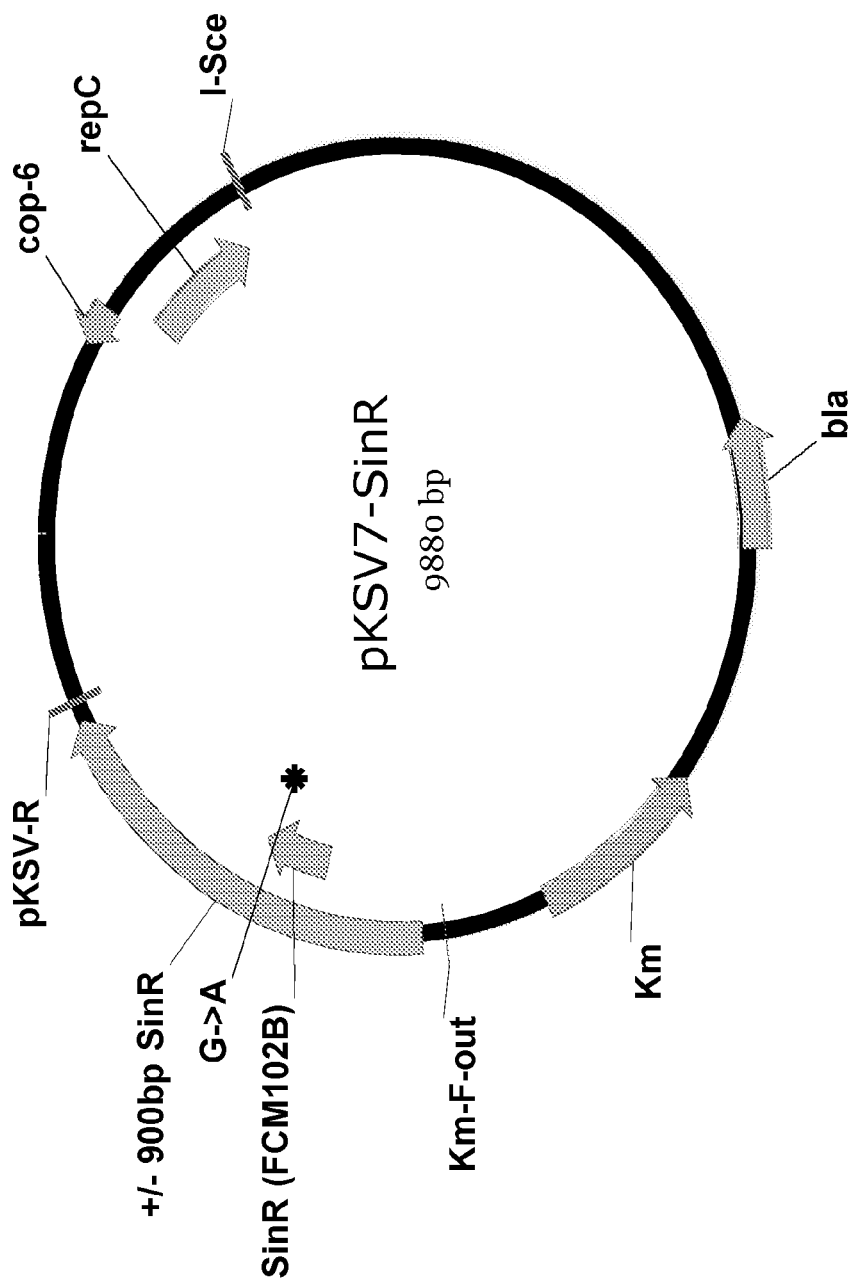
FIG. 1 shows a schematic of the plasmid map of pKSV7-sinR.

The present invention generally relates to bacterial cells having one or more genetic alterations that result in increased expression of a protein of interest (hereinafter, a "POI") and methods of making and using such cells Before the present compositions and methods are described in greater detail, it is to be understood that the present compositions and methods are not limited to particular embodiments described, as such may, of course, vary. It is also to be understood that the terminology used herein is for the purpose of describing particular embodiments only, and is not intended to be limiting, since the scope of the present compositions and methods will be limited only by the appended claims.

Where a range of values are provided, it is understood that each intervening value, to the tenth of the unit of the lower limit unless the context clearly dictates otherwise, between the upper and lower limit of that range and any other stated or intervening value in that stated range, is encompassed within the present compositions and methods. The upper and lower limits of these smaller ranges may independently be included in the smaller ranges and are also encompassed within the present compositions and methods, subject to any specifically excluded limit in the stated range. Where the stated range includes one or both of the limits, ranges excluding either or both of those included limits are also included in the present compositions and methods.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number. For example, in connection with a numerical value, the term "about" refers to a range of −10% to +10% of the numerical value, unless the term is otherwise specifically defined in context. In another example, the phrase a "pH value of about 6" refers to pH values of from 5.4 to 6.6, unless the pH value is specifically defined otherwise.

The headings provided herein are not limitations of the various aspects or embodiments of the present compositions and methods which can be had by reference to the specification as a whole. Accordingly, the terms defined immediately below are more fully defined by reference to the specification as a whole.

The present document is organized into a number of sections for ease of reading; however, the reader will appreciate that statements made in one section may apply to other sections. In this manner, the headings used for different sections of the disclosure should not be construed as limiting.

Unless defined otherwise, all technical and scientific terms used herein have the same meaning as commonly understood by one of ordinary skill in the art to which the present compositions and methods belongs. Although any methods and materials similar or equivalent to those described herein can also be used in the practice or testing of the present compositions and methods, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present compositions and methods are not entitled to antedate such publication by virtue of prior invention. Further, the dates of publication provided may be different from the actual publication dates which may need to be independently confirmed.

In accordance with this detailed description, the following abbreviations and definitions apply. Note that the singular forms "a," "an," and "the" include plural referents unless the context clearly dictates otherwise. Thus, for example, reference to "an enzyme" includes a plurality of such enzymes, and reference to "the dosage" includes reference to one or more dosages and equivalents thereof known to those skilled in the art, and so forth.

It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is further noted that the term "consisting essentially of," as used herein refers to a composition where the component(s) after the term is in the presence of other known component(s) in a total amount that is less than 30% by weight of the total composition and do not contribute to or interferes with the actions or activities of the component(s).

It is further noted that the term "comprising," as used herein, means including, but not limited to, the component(s) after the term "comprising." The component(s) after the term "comprising" are required or mandatory, but the composition comprising the component(s) may further include other non-mandatory or optional component(s).

It is also noted that the term "consisting of," as used herein, means including, and limited to, the component(s) after the term "consisting of." The component(s) after the term "consisting of" are therefore required or mandatory, and no other component(s) are present in the composition.

As will be apparent to those of skill in the art upon reading this disclosure, each of the individual embodiments described and illustrated herein has discrete components and features which may be readily separated from or combined with the features of any of the other several embodiments without departing from the scope or spirit of the present compositions and methods described herein. Any recited method can be carried out in the order of events recited or in any other order which is logically possible.

Definitions

The present invention generally relates to Gram positive bacterial cells (and methods of making and using the same) that have been altered (or modified) to have an increased capacity to express and/or produce one or more proteins of interest.

As defined herein, a "modified cell", an "altered cell", a "modified bacterial cell", an "altered bacterial cell", a "modified host cell", or an "altered host cell" may be used interechangeably and refer to recombinant Gram positive bacterial cells that contain at least one genetic alteration that alters or changes the expression (i.e., an increase in expression or a decrease in expression) of one or more genes of the sin operon. For example, an "altered" Gram positive bacterial cell of the instant disclosure may be further defined as an "altered cell" which is derived from a parental bacterial cell, wherein the altered (daughter) cell comprises at least one genetic alteration that reduces expression of one or more genes in the sin operon.

As defined herein, an "unmodified cell", an "unaltered cell", an "unmodified bacterial cell", an "unaltered bacterial cell", an "unmodified host cell", or an "unaltered host cell" may be used interechangeably and refer to "unaltered" 'parental' Gram positive bacterial cells that do not comprises the at least one genetic alteration that reduces the expression of one or more genes of the sin operon. In certain embodiments, an unaltered Gram positive bacterial cell is refered to as a "control cell" or an "unaltered Gram positive bacterial 'control' cell".

For example, certain embodiments of the disclosure are directed to "altered" Gram positive bacterial cells expressing an increased amount of a POI, wherein the increased amount of the POI is relative to the expression of the same POI in an "unaltered" Gram positive bacterial cell (i.e., an unaltered Gram positive bacterial "control" cell.

Thus, as defined herein, when the terms or phrases "unaltered bacterial cell(s)", "unaltered Gram positive bacterial cell(s)", "unaltered Gram positive bacterial 'control' cell(s)" and the like are used in the context of comparison to the one or more "altered bacterial cells" of the disclosure, it is understood that both the altered (daughter) cells and the unaltered parental (control) cells are grown/cultured under essentially identical conditions and media.

As defined herein, the sin (sporulation innhibition) operon comprises at least a polynucleotide encoding the sinI (Inhibitor of sinR) protein and a polynucleotide encoding the sinR (Repressor) protein, and may further include 5' and 3' regulatory nucleotide sequences operably linked or interspersed with the sinR and/or sinI genes or polynucleotide sequences thereof (see, e.g., Gaur et al., *J Bacteriol* 168: 860-869, 1986). In certain embodiments, a sinR gene (or a sinR polynucleotide derived from a sinR gene) of the sin operon comprises at least 60% nucleic acid sequence identity to the sinR polynucleotide of SEQ ID NO: 1.

As used herein, an "operon" comprises a group of contiguous genes that can be transcribed as a single transcription unit from a common promoter, and are thereby subject to co-regulation. In some embodiments, an operon may include multiple promoters that drive the transcription of multiple different mRNAs (see, e.g., the promoters in the phd operon schematized in FIG. 1).

As defined herein, the terms "increased expression", "increased expression of a POI", "increased production", "increased production of a POI" and the like refers to an "altered" (daughter) bacterial cell comprising at least one genetic alteration that reduces the expression of one or more genes of the sin operon, wherein the "increase" is always relative (vis-á-vis) to an "unaltered" (parental) bacterial (control) cell expressing the same POI.

As defined herein, the term "introducing", as used in phrases such as "introducing into the bacterial cell" at least one polynucleotide open reading frame (ORF), or a gene thereof, or a vector thereof, includes methods known in the art for introducing polynucleotides into a cell, including, but not limited to protoplast fusion, transformation (e.g., calcium chloride, electroporation), transduction, transfection, conjugation and the like (see e.g., Ferrari et al., "*Genetics*," in Hardwood et al, (eds.), *Bacillus*, Plenum Publishing Corp., pages 57-72, 1989).

As defined herein, the term "open reading frame" (hereinafter, "ORF") means a nucleic acid or nucleic acid sequence (whether naturally occurring, non-naturally occurring, or synthetic) comprising an uninterrupted reading frame consisting of (i) an initiation codon, (ii) a series of two (2) of more codons representing amino acids, and (iii) a termination codon, the ORF being read (or translated) in the 5' to 3' direction.

It is understood that the polynucleotides described herein include "genes" and that the nucleic acid molecules described herein include "vectors" or "plasmids". Accordingly, the term "gene", refers to a polynucleotide that codes for a particular sequence of amino acids, which comprise all, or part of a protein, and may include regulatory (non-transcribed) DNA sequences, such as promoter sequences, which determine for example the conditions under which the gene is expressed. The transcribed region of the gene may include untranslated regions (UTRs), including introns, 5'-untranslated region (UTR), and 3'-UTR, as well as the coding sequence.

The term "promoter" as used herein refers to a nucleic acid sequence capable of controlling the expression of a coding sequence or functional RNA. In general, a coding sequence is located 3' (downstream) to a promoter sequence. Promoters may be derived in their entirety from a native gene, or be composed of different elements derived from different promoters found in nature, or even comprise synthetic nucleic acid segments. It is understood by those skilled in the art that different promoters may direct the expression of a gene in different cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "operably linked" as used herein refers to the association of nucleic acid sequences on a single nucleic acid fragment so that the function of one is affected by the other. For example, a promoter is operably linked with a coding sequence when it is capable of effecting the expression of that coding sequence (i.e., that the coding sequence is under the transcriptional control of the promoter). Coding sequences can be operably linked to regulatory sequences in sense or antisense orientation.

A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that are not episomal in nature, or it can be an organism which comprises one or more of the above polynucleotide constructs such as an *agrobacterium* or a *bacterium*.

As defined herein, term "expression" or "expressed" with respect to a gene sequence, an ORF sequence or polynucleotide sequence, refers to transcription of the gene, ORF or polynucleotide and, as appropriate, translation of the resulting mRNA transcript to a protein. Thus, as will be clear from the context, expression of a protein results from transcription and translation of the open reading frame sequence. The level of expression of a desired product in a host microorganism may be determined on the basis of either the amount of corresponding mRNA that is present in the host, or the amount of the desired product encoded by the selected sequence. For example, mRNA transcribed from a selected sequence can be quantitated by PCR or by northern hybridization (see Sambrook et al., Molecular Cloning: A Laboratory Manual, Cold Spring Harbor Laboratory Press, 1989). Protein encoded by a selected sequence can be quantitated by various methods (e.g., by ELISA, by assaying for the biological activity of the protein, or by employing assays that are independent of such activity, such as western blotting or radioimmunoassay, using antibodies that are recognize and bind reacting the protein). the term "expression" in the context of a gene (or polynucleotide thereof), is the process by which a protein is produced based on the nucleic acid sequence of the gene (or polynucleotide thereof), and thus includes both transcription and translation.

As defined herein, a messeger RNA (mRNA) transcript derived from the sin operon at least includes an mRNA transcript encoding all or a portion of the sinR protein.

As defined herein, a "genetic alteration" that reduces the expression of one or more genes of the sin operon includes, but is not limited to, a missense mutation, a frameshift mutation, a nonsense mutation, an insertion mutation, a deletion mutation and the like.

The term "mutation" as used herein indicates any modification of a nucleic acid which results in an altered nucleic acid or encoded polypeptide (i.e., relative to the wild-type nucleic acid or polypeptide sequence). Mutations include alterations arising within a protein-encoding region of a gene, as well as alterations in regions outside of a protein-encoding sequence, such as, but not limited to, regulatory or promoter sequences. Thus, a genetic alteration may be a mutation of any type.

In certain embodiments, a portion of a genetically altered (modified) microorganism's genome may be replaced with one or more heterologous (exogenous) polynucleotides.

As used herein, "the genus *Bacillus*" or "a member of the *Bacillus* genus" includes all species within the genus "*Bacil-*

*lus*," as known to those of skill in the art, including but not limited to *B. subtilis, B. licheniformis, B. lentus, B. brevis, B. stearothermophilus, B. alkalophilus, B. amyloliquefaciens, B. clausii, B. sonorensis, B. halodurans, B. pumilus, B. lautus, B. pabuli, B. cereus, B. agaradhaerens, B akibai, B. clarkii, B. pseudofirmus, B. lehensis, B. megaterium, B. coagulans, B. circulans, B. gibsonii,* and *B. thuringiensis.*

It is recognized that the genus *Bacillus* continues to undergo taxonomical reorganization. Thus, it is intended that the genus include species that have been reclassified, including but not limited to such organisms as *B. stearothermophilus,* which is now named "*Geobacillus stearothermophilus.*" The production of resistant endospores in the presence of oxygen is considered the defining feature of the genus *Bacillus,* although this characteristic also applies to the recently named *Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus,* and *Virgibacillus.*

As used herein, "nucleic acid" refers to a nucleotide or polynucleotide sequence, and fragments or portions thereof, as well as to DNA, cDNA, and RNA of genomic or synthetic origin which may be double-stranded or single-stranded, whether representing the sense or antisense strand. It will be understood that as a result of the degeneracy of the genetic code, a multitude of nucleotide sequences may encode a given protein.

As used herein, the term "vector" is any means by which a nucleic acid can be propagated and/or transferred between organisms, cells, or cellular components. Vectors include viruses, bacteriophage, pro-viruses, plasmids, phagemids, transposons, and artificial chromosomes such as YACs (yeast artificial chromosomes), BACs (bacterial artificial chromosomes), and PLACs (plant artificial chromosomes), and the like, that are "episomes", that is, that replicate autonomously or can integrate into a chromosome of a host microorganism. An "expression vector" refers to a vector that has the ability to incorporate and express heterologous DNA in a foreign cell. Many prokaryotic and eukaryotic expression vectors are commercially available. A "targeting vector" is a vector that includes polynucleotide sequences that are homologus to a region in the choromosome of a host cell into which it is transformed and that can drive homologous recombination at that region. Targetting vectors find use in introducing mutations into the chromosome of a cell through homologous recombination. In some embodiments, the targeting vector comprises comprises other non-homologous sequences, e.g., added to the ends (i.e., stuffer sequences or flanking sequences). The ends can be closed such that the targeting vector forms a closed circle, such as, for example, insertion into a vector. Selection and/or construction of appropriate vectors is within the knowledge of those having skill in the art.

As used herein, the term "plasmid" refers to a circular double-stranded (ds) DNA construct used as a cloning vector, and which forms an extrachromosomal self-replicating genetic element in many bacteria and some eukaryotes. In some embodiments, plasmids become incorporated into the genome of the host cell.

By "purified" or "isolated" or "enriched" is meant that a biomolecule (e.g., a polypeptide or polynucleotide) is altered from its natural state by virtue of separating it from some or all of the naturally occurring constituents with which it is associated in nature. Such isolation or purification may be accomplished by art-recognized separation techniques such as ion exchange chromatography, affinity chromatography, hydrophobic separation, dialysis, protease treatment, ammonium sulphate precipitation or other protein salt precipitation, centrifugation, size exclusion chromatography, filtration, microfiltration, gel electrophoresis or separation on a gradient to remove whole cells, cell debris, impurities, extraneous proteins, or enzymes undesired in the final composition. It is further possible to then add constituents to a purified or isolated biomolecule composition which provide additional benefits, for example, activating agents, anti-inhibition agents, desirable ions, compounds to control pH or other enzymes or chemicals.

As used herein, the terms "selectable marker" or "selective marker" refer to a nucleic acid (e.g., a gene) capable of expression in host cell which allows for ease of selection of those hosts containing the nucleic acid. Examples of such selectable markers include but are not limited to antimicrobials. Thus, the term "selectable marker" refers to genes that provide an indication that a host cell has taken up an incoming DNA of interest or some other reaction has occurred. Typically, selectable markers are genes that confer antimicrobial resistance or a metabolic advantage on the host cell to allow cells containing the exogenous DNA to be distinguished from cells that have not received any exogenous sequence during the transformation. Other markers useful in accordance with the invention include, but are not limited to auxotrophic markers, such as tryptophan; and detection markers, such as β-galactosidase.

"Inactivation" of a gene means that the expression of a gene or the activity of its encoded biomolecule is blocked or is otherwise unable to exert its known function. Inactivation can occur via any suitable means, e.g., via a genetic alteration as described above. In one embodiment, the expression product of an inactivated gene is a truncated protein with a corresponding change in the biological activity of the protein. In some embodiments, an altered Gram positive bactarial strain comprises inactivation of one or more genes that results preferably in stable and non-reverting inactivation.

In some embodiments, inactivation is achieved by deletion. In some embodiments, the region targeted for deletion (e.g., a gene) is deleted by homologous recombination. For example, a DNA construct comprising an incoming sequence having a selective marker flanked on each side by sequences that are homologous to the region targeted for deletion is used (where the sequences may be referred to herein as a "homology box"). The DNA construct aligns with the homologous sequences of the host chromosome and in a double crossover event the region targeted fot deletion is excised out of the host chromosome.

An "insertion" or "addition" is a change in a nucleotide or amino acid sequence which has resulted in the addition of one or more nucleotides or amino acid residues, respectively, as compared to the naturally occurring or parental sequence.

As used herein, a "substitution" results from the replacement of one or more nucleotides or amino acids by different nucleotides or amino acids, respectively.

Methods of mutating genes are well known in the art and include but are not limited to site-directed mutation, generation of random mutations, and gapped-duplex approaches (See e.g., U.S. Pat. No. 4,760,025; Moring et al., Biotech. 2:646, 1984; and Kramer et al., Nucleic Acids Res., 12:9441, 1984).

As used herein, "homologous genes" refers to a pair of genes from different, but usually related species, which correspond to each other and which are identical or very similar to each other. The term encompasses genes that are separated by speciation (i.e., the development of new species) (e.g., orthologous genes), as well as genes that have been separated by genetic duplication (e.g., paralogous genes).

As used herein, "ortholog" and "orthologous genes" refer to genes in different species that have evolved from a common ancestral gene (i.e., a homologous gene) by speciation. Typically, orthologs retain the same function in during the course of evolution. Identification of orthologs finds use in the reliable prediction of gene function in newly sequenced genomes.

As used herein, "paralog" and "paralogous genes" refer to genes that are related by duplication within a genome. While orthologs retain the same function through the course of evolution, paralogs evolve new functions, even though some functions are often related to the original one. Examples of paralogous genes include, but are not limited to genes encoding trypsin, chymotrypsin, elastase, and thrombin, which are all serine proteinases and occur together within the same species.

As used herein, "homology" refers to sequence similarity or identity, with identity being preferred. This homology is determined using standard techniques known in the art (See e.g., Smith and Waterman, Adv. Appl. Math., 2:482 [1981]; Needleman and Wunsch, J. Mol. Biol., 48:443 [1970]; Pearson and Lipman, Proc. Natl. Acad. Sci. USA 85:2444 [1988]; programs such as GAP, BESTFIT, FASTA, and TFASTA in the Wisconsin Genetics Software Package (Genetics Computer Group, Madison, Wis.); and Devereux et al., Nucl. Acid Res., 12:387-395 [1984]).

As used herein, an "analogous sequence" is one wherein the function of the gene is essentially the same as the gene designated from *Bacillus subtilis* strain 168. Additionally, analogous genes include at least 60%, 65%, 70%, 75%, 80%, 85%, 90%, 95%, 97%, 98%, 99% or 100% sequence identity with the sequence of the *Bacillus subtilis* strain 168 gene. Alternately, analogous sequences have an alignment of between 70 to 100% of the genes found in the *B. subtilis* 168 region and/or have at least between 5-10 genes found in the region aligned with the genes in the *B. subtilis* 168 chromosome. In additional embodiments more than one of the above properties applies to the sequence. Analogous sequences are determined by known methods of sequence alignment. A commonly used alignment method is BLAST, although as indicated above and below, there are other methods that also find use in aligning sequences.

One example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng and Doolittle (Feng and Doolittle, J. Mol. Evol., 35:351-360 [1987]). The method is similar to that described by Higgins and Sharp (Higgins and Sharp, CABIOS 5:151-153 [1989]). Useful PILEUP parameters including a default gap weight of 3.00, a default gap length weight of 0.10, and weighted end gaps.

Another example of a useful algorithm is the BLAST algorithm, described by Altschul et al., (Altschul et al., J. Mol. Biol., 215:403-410, [1990]; and Karlin et al., Proc. Natl. Acad. Sci. USA 90:5873-5787 [1993]). A particularly useful BLAST program is the WU-BLAST-2 program (See, Altschul et al., Meth. Enzymol., 266:460-480 [1996]). WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched. However, the values may be adjusted to increase sensitivity. A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

As used herein, "percent (%) sequence identity" with respect to the amino acid or nucleotide sequences identified herein is defined as the percentage of amino acid residues or nucleotides in a candidate sequence that are identical with the amino acid residues or nucleotides in a sequence of interest, after aligning the sequences and introducing gaps, if necessary, to achieve the maximum percent sequence identity, and not considering any conservative substitutions as part of the sequence identity.

By "homologue" (or "homolog") shall mean an entity having a specified degree of identity with the subject amino acid sequences and the subject nucleotide sequences. A homologous sequence is can include an amino acid sequence that is at least 60%, 65%, 70%, 75%, 80%, 85%, 86%, 87%, 88%, 89%, 90%, 91%, 92%, 93%, 94%, 95%, 96%, 97%, 98% or even 99% identical to the subject sequence, using conventional sequence alignment tools (e.g., Clustal, BLAST, and the like). Typically, homologues will include the same active site residues as the subject amino acid sequence, unless otherwise specified.

Methods for performing sequence alignment and determining sequence identity are known to the skilled artisan, may be performed without undue experimentation, and calculations of identity values may be obtained with definiteness. See, for example, Ausubel et al., eds. (1995) *Current Protocols in Molecular Biology*, Chapter 19 (Greene Publishing and Wiley-Interscience, New York); and the ALIGN program (Dayhoff (1978) in *Atlas of Protein Sequence and Structure* 5: Suppl. 3 (National Biomedical Research Foundation, Washington, D.C.). A number of algorithms are available for aligning sequences and determining sequence identity and include, for example, the homology alignment algorithm of Needleman et al. (1970) *J. Mol. Biol.* 48:443; the local homology algorithm of Smith et al. (1981) *Adv. Appl. Math.* 2:482; the search for similarity method of Pearson et al. (1988) *Proc. Natl. Acad. Sci.* 85:2444; the Smith-Waterman algorithm (*Meth. Mol. Biol.* 70:173-187 (1997); and BLASTP, BLASTN, and BLASTX algorithms (see Altschul et al. (1990) *J. Mol. Biol.* 215:403-410).

Computerized programs using these algorithms are also available, and include, but are not limited to: ALIGN or Megalign (DNASTAR) software, or WU-BLAST-2 (Altschul et al., Meth. Enzym., 266:460-480 (1996)); or GAP, BESTFIT, BLAST, FASTA, and TFASTA, available in the Genetics Computing Group (GCG) package, Version 8, Madison, Wis., USA; and CLUSTAL in the PC/Gene program by Intelligenetics, Mountain View, Calif. Those skilled in the art can determine appropriate parameters for measuring alignment, including algorithms needed to achieve maximal alignment over the length of the sequences being compared. Preferably, the sequence identity is determined using the default parameters determined by the program. Specifically, sequence identity can determined by using Clustal W (Thompson J. D. et al. (1994) Nucleic Acids Res. 22:4673-4680) with default parameters, i.e.:

| | |
|---|---|
| Gap opening penalty: | 10.0 |
| Gap extension penalty: | 0.05 |
| Protein weight matrix: | BLOSUM series |
| DNA weight matrix: | IUB |
| Delay divergent sequences %: | 40 |
| Gap separation distance: | 8 |
| DNA transitions weight: | 0.50 |
| List hydrophilic residues: | GPSNDQEKR |
| Use negative matrix: | OFF |
| Toggle Residue specific penalties: | ON |
| Toggle hydrophilic penalties: | ON |
| Toggle end gap separation penalty | OFF |

As used herein, the term "hybridization" refers to the process by which a strand of nucleic acid joins with a complementary strand through base pairing, as known in the art.

A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature (Tm) of the nucleic acid binding complex or probe. For example, "maximum stringency" typically occurs at about Tm−5° C. (5° below the Tm of the probe); "high stringency" at about 5-10° C. below the Tm; "intermediate stringency" at about 10-20° C. below the Tm of the probe; and "low stringency" at about 20-25° C. below the Tm. Functionally, maximum stringency conditions may be used to identify sequences having strict identity or near-strict identity with the hybridization probe; while an intermediate or low stringency hybridization can be used to identify or detect polynucleotide sequence homologs.

Moderate and high stringency hybridization conditions are well known in the art. An example of high stringency conditions includes hybridization at about 42° C. in 50% formamide, 5×SSC, 5×Denhardt's solution, 0.5% SDS and 100 μg/ml denatured carrier DNA followed by washing two times in 2×SSC and 0.5% SDS at room temperature and two additional times in 0.1×SSC and 0.5% SDS at 42° C. An example of moderate stringent conditions include an overnight incubation at 37° C. in a solution comprising 20% formamide, 5×SSC (150 mM NaCl, 15 mM trisodium citrate), 50 mM sodium phosphate (pH 7.6), 5×Denhardt's solution, 10% dextran sulfate and 20 mg/ml denatured sheared salmon sperm DNA, followed by washing the filters in 1×SSC at about 37-50° C. Those of skill in the art know how to adjust the temperature, ionic strength, etc. as necessary to accommodate factors such as probe length and the like.

The term "recombinant," when used in reference to a biological component or composition (e.g., a cell, nucleic acid, polypeptide/enzyme, vector, etc.) indicates that the biological component or composition is in a state that is not found in nature. In other words, the biological component or composition has been modified by human intervention from its natural state. For example, a recombinant cell encompass a cell that expresses one or more genes that are not found in its native parent (i.e., non-recombinant) cell, a cell that expresses one or more native genes in an amount that is different than its native parent cell, and/or a cell that expresses one or more native genes under different conditions than its native parent cell. Recombinant nucleic acids may differ from a native sequence by one or more nucleotides, be operably linked to heterologous sequences (e.g., a heterologous promoter, a sequence encoding a non-native or variant signal sequence, etc.), be devoid of intronic sequences, and/or be in an isolated form. Recombinant polypeptides/enzymes may differ from a native sequence by one or more amino acids, may be fused with heterologous sequences, may be truncated or have internal deletions of amino acids, may be expressed in a manner not found in a native cell (e.g., from a recombinant cell that over-expresses the polypeptide due to the presence in the cell of an expression vector encoding the polypeptide), and/or be in an isolated form. It is emphasized that in some embodiments, a recombinant polynucleotide or polypeptide/enzyme has a sequence that is identical to its wild-type counterpart but is in a non-native form (e.g., in an isolated or enriched form).

As used herein, the term "target sequence" refers to a DNA sequence in the host cell that encodes the sequence where it is desired for the incoming sequence to be inserted into the host cell genome. In some embodiments, the target sequence encodes a functional wild-type gene or operon, while in other embodiments the target sequence encodes a functional mutant gene or operon, or a non-functional gene or operon.

As used herein, a "flanking sequence" refers to any sequence that is either upstream or downstream of the sequence being discussed (e.g., for genes A-B-C, gene B is flanked by the A and C gene sequences). In a embodiment, the incoming sequence is flanked by a homology box on each side. In another embodiment, the incoming sequence and the homology boxes comprise a unit that is flanked by stuffer sequence on each side. In some embodiments, a flanking sequence is present on only a single side (either 3' or 5'), but in embodiments, it is on each side of the sequence being flanked. The sequence of each homology box is homologous to a sequence in the *Bacillus* chromosome. These sequences direct where in the *Bacillus* chromosome the new construct gets integrated and what part of the *Bacillus* chromosome will be replaced by the incoming sequence. In a embodiment, the 5' and 3' ends of a selective marker are flanked by a polynucleotide sequence comprising a section of the inactivating chromosomal segment. In some embodiments, a flanking sequence is present on only a single side (either 3' or 5'), while in embodiments, it is present on each side of the sequence being flanked.

As used herein, the terms "amplifiable marker," "amplifiable gene," and "amplification vector" refer to a gene or a vector encoding a gene which permits the amplification of that gene under appropriate growth conditions.

"Template specificity" is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (See e.g., Kacian et al., Proc. Natl. Acad. Sci. USA 69:3038 [1972]). Other nucleic acids are not replicated by this amplification enzyme. Similarly, in the case of T7 RNA polymerase, this amplification enzyme has a stringent specificity for its own promoters (See, Chamberlin et al., Nature 228:227 [1970]). In the case of T4 DNA ligase, the enzyme will not ligate the two oligonucleotides or polynucleotides, where there is a mismatch between the oligonucleotide or polynucleotide substrate and the template at the ligation junction (See, Wu and Wallace, Genomics 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences.

As used herein, the term "amplifiable nucleic acid" refers to nucleic acids which may be amplified by any amplification method. It is contemplated that "amplifiable nucleic acid" will usually comprise "sample template."

As used herein, the term "sample template" refers to nucleic acid originating from a sample which is analyzed for the presence of "target" (defined below). In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the term "polymerase chain reaction" ("PCR") refers to the methods of U.S. Pat. Nos. 4,683,195 4,683,202, and 4,965,188, hereby incorporated by reference, which include methods for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "RT-PCR" refers to the replication and amplification of RNA sequences. In this method, reverse transcription is coupled to PCR, most often using a one enzyme procedure in which a thermostable polymerase is employed, as described in U.S. Pat. No. 5,322,770, herein incorporated by reference. In RT-PCR, the RNA template is converted to cDNA due to the reverse transcriptase activity of the polymerase, and then amplified using the polymerizing activity of the polymerase (i.e., as in other PCR methods).

As used herein, "genetically altered host strain" (e.g., agenetically altered *Bacillus* strain) refers to a genetically engineered host cell, also called a recombinant host cell. In some embodiments, the genetically altered host cell has enhanced (increased) expression of a protein of interest as compared to the expression and/or production of the same protein of interest in a corresponding unaltered host strain grown under essentially the same growth conditions. In some embodiments, the enhanced level of expression results from reduced expression of one or more gene from the sin operon, e.g., the sinR gene. In some embodiments, the altered strains are genetically engineered *Bacillus* sp. having one or more deleted endogenous chromosomal regions or fragments thereof, where a protein of interest has an enhanced level of expression or production, as compared to a corresponding unaltered *Bacillus* host strain grown under essentially the same growth conditions.

As used herein, the term "chromosomal integration" refers to the process whereby the incoming sequence is introduced into the chromosome of a host cell (e.g., *Bacillus*). The homologous regions of the transforming DNA align with homologous regions of the chromosome. Subsequently, the sequence between the homology boxes is replaced by the incoming sequence in a double crossover (i.e., homologous recombination). In some embodiments of the present invention, homologous sections of an inactivating chromosomal segment of a DNA construct align with the flanking homologous regions of the indigenous chromosomal region of the *Bacillus* chromosome. Subsequently, the indigenous chromosomal region is deleted by the DNA construct in a double crossover (i.e., homologous recombination).

"Homologous recombination" means the exchange of DNA fragments between two DNA molecules or paired chromosomes at the site of identical or nearly identical nucleotide sequences. In a embodiment, chromosomal integration is homologous recombination.

"Homologous sequences" as used herein means a nucleic acid or polypeptide sequence having 100%, 99%, 98%, 97%, 96%, 95%, 94%, 93%, 92%, 91%, 90%, 88%, 85%, 80%, 75%, or 70% sequence identity to another nucleic acid or polypeptide sequence when optimally aligned for comparison. In some embodiments, homologous sequences have between 85% and 100% sequence identity, while in other embodiments there is between 90% and 100% sequence identity, and in more embodiments, there is 95% and 100% sequence identity.

As used herein "amino acid" refers to peptide or protein sequences or portions thereof. The terms "protein", "peptide" and "polypeptide" are used interchangeably.

As used herein, "protein of interest" and "polypeptide of interest" refer to a protein/polypeptide that is desired and/or being assessed. In some embodiments, the protein of interest is intracellular, while in other embodiments, it is a secreted polypeptide.

Particularly polypeptides include enzymes, including, but not limited to those selected from amylolytic enzymes, proteolytic enzymes, cellulytic enzymes, oxidoreductase enzymes and plant cell-wall degrading enzymes. More particularly, these enzyme include, but are not limited to amylases, proteases, xylanases, lipases, laccases, phenol oxidases, oxidases, cutinases, cellulases, hemicellulases, esterases, peroxidases, catalases, glucose oxidases, phytases, pectinases, perhydrolases, polyol oxidases, pectate lyases, glucosidases, isomerases, transferases, galactosidases and chitinases. In particular embodiments of the present invention, the polypeptide of interest is a protease. In some embodiments, the protein of interest is a secreted polypeptide which is fused to a signal peptide (i.e., an amino-terminal extension on a protein to be secreted). Nearly all secreted proteins use an amino-terminal protein extension which plays a crucial role in the targeting to and translocation of precursor proteins across the membrane. This extension is proteolytically removed by a signal peptidase during or immediately following membrane transfer.

In some embodiments of the present invention, the polypeptide of interest is selected from hormones, antibodies, growth factors, receptors, etc. Hormones encompassed by the present invention include but are not limited to, follicle-stimulating hormone, luteinizing hormone, corticotropin-releasing factor, somatostatin, gonadotropin hormone, vasopressin, oxytocin, erythropoietin, insulin and the like. Growth factors include, but are not limited to platelet-derived growth factor, insulin-like growth factors, epidermal growth factor, nerve growth factor, fibroblast growth factor, transforming growth factors, cytokines, such as interleukins (e.g., IL-1 through IL-13), interferons, colony stimulating factors, and the like. Antibodies include but are not limited to immunoglobulins obtained directly from any species from which it is desirable to produce antibodies. In addition, the present invention encompasses modified antibodies. Polyclonal and monoclonal antibodies are also encompassed by the present invention. In particularly embodiments, the antibodies are human antibodies.

As used herein, a "derivative" or "variant" of a polypeptide means a polypeptide, which is derived from a precursor polypeptide (e.g., the native polypeptide) by addition of one or more amino acids to either or both the C- and N-terminal ends, substitution of one or more amino acids at one or a number of different sites in the amino acid sequence, deletion of one or more amino acids at either or both ends of the polypeptide or at one or more sites in the amino acid sequence, insertion of one or more amino acids at one or more sites in the amino acid sequence, and any combination thereof. The preparation of a derivative or variant of a polypeptide may be achieved in any convenient manner, e.g., by modifying a DNA sequence which encodes the native polypeptides, transformation of that DNA sequence into a suitable host, and expression of the modified DNA sequence to form the derivative/variant polypeptide. Derivatives or variants further include polypeptides that are chemically modified.

As used herein, the term "heterologous protein" refers to a protein or polypeptide that does not naturally occur in the host cell. Examples of heterologous proteins include enzymes such as hydrolases including proteases, cellulases, amylases, carbohydrases, and lipases; isomerases such as racemases, epimerases, tautomerases, or mutases; transferases, kinases and phophatases. In some embodiments, the proteins are therapeutically significant proteins or peptides, including but not limited to growth factors, cytokines, ligands, receptors and inhibitors, as well as vaccines and antibodies. In additional embodiments, the proteins are commercially important industrial proteins/peptides (e.g., proteases, carbohydrases such as amylases and glucoamylases, cellulases, oxidases and lipases). In some embodiments, the genes encoding the proteins are naturally occurring genes, while in other embodiments, mutated and/or synthetic genes are used.

As used herein, "homologous protein" refers to a protein or polypeptide native or naturally occurring in a cell. In embodiments, the cell is a Gram-positive cell, while in particularly embodiments, the cell is a *Bacillus* host cell. In alternative embodiments, the homologous protein is a native protein produced by other organisms, including but not limited to *E. coli*. The invention encompasses host cells producing the homologous protein via recombinant DNA technology.

The present invention relates in general to bacterial cells having a genetic alteration that results in increased expression of a protein of interest and methods of making and using such cells. Aspects of the present invention include Gram-positive microorganisms, such as *Bacillus* species, having a genetic alteration that reduces the expression of a gene in the sin operon and results in enhanced expression of a protein of interest (e.g., reduction in the expression of the sinR gene).

As summarized above, aspects of the invention include methods for increasing expression of a protein of interest from a Gram positive bacterial cell and is based on the observation that the production of a protein of interest is increased in Gram positive cells that have been genetically altered to have reduced expression of one or more genes in the sin operon is as compared to the expression level of the same protein of interest in a corresponding non-genetically altered Gram positive cell (e.g., a wild type and/or a parental cell). By genetic alteration is meant any alteration in a host cell that changes the genetic make-up of the host cell, for example by episomal addition and/or chromosomal insertion, deletion, inversion, base change, etc. No limitation in this regard is intended.

In certain embodiments, the method involves producing or obtaining an altered Gram positive bacterial cell that comprises at least one genetic alteration that reduces expression of one or more genes in the sin operon and that is capable of producing a protein of interest and culturing the altered Gram positive bacterial cell under conditions such that the protein of interest is expressed by the altered Gram positive bacterial cell. Expression of the protein of interest is thereby increased in the altered Gram positive bacterial cell compared to the expression of the protein of interest in a corresponding unaltered Gram positive bacterial cell grown under essentially the same culture conditions.

According to certain embodiments, the genetically altered Gram positive bacterial cell (or parental cell from which the genetically altered Gram positive bacterial cell is produced) can be a *Bacillus* strain. In some embodiments, the *Bacillus* strain of interest is alkalophilic. Numerous alkalophilic *Bacillus* strains are known (See e.g., U.S. Pat. No. 5,217,878; and Aunstrup et al., Proc IV IFS: Ferment. Technol. Today, 299-305 [1972]). In some embodiments, the *Bacillus* strain of interest is an industrial *Bacillus* strain. Examples of industrial *Bacillus* strains include, but are not limited to *B. licheniformis*, *B. lentus*, *B. subtilis* and *B. amyloliquefaciens*. In additional embodiments, the *Bacillus* host strain is selected from the group consisting of *B. lentus*, *B. brevis*, *B. stearothermophilus*, *B. alkalophilus*, *B. coagulans*, *B. circulans*, *B. pumilus*, *B. thuringiensis*, *B. clausii*, and *B. megaterium*, as well as other organisms within the genus *Bacillus*, as discussed above. In particular embodiments, *B. subtilis* is used. For example, U.S. Pat. Nos. 5,264,366 and 4,760,025 (RE 34,606) describe various *Bacillus* host strains that find use in the present invention, although other suitable strains are contemplated for use in the present invention.

The parental strain of a genetically altered cell as dieschribed herein (e.g., a parental *Bacillus* strain) may be an industrial strain, which includes non-recombinant strains, mutant strains of a naturally occurring strain, or a recombinant strain. In certain embodiments, the parental strain is a recombinant host strain wherein a polynucleotide encoding a polypeptide of interest has been introduced into the host. While the introduction of a polynucleotide encoding a polypeptide of interest may be done in a parental strain, this step may also be performed in a strain that has already been genetically altered for increased polypeptide production as detailed herein. In some embodiments, the host strain is a *Bacillus subtilis* host strain, e.g., a recombinant *B. subtilis* host strain.

Numerous *B. subtilis* strains are known that find use in aspects of the present invention, including but not limited to 1A6 (ATCC 39085), 168 (1A01), SB19, W23, Ts85, B637, PB1753 through PB1758, PB3360, JH642, 1A243 (ATCC 39,087), ATCC 21332, ATCC 6051, MI113, DE100 (ATCC 39,094), GX4931, PBT 110, and PEP 211 strain (See e.g., Hoch et al., Genetics, 73:215-228 [1973]; U.S. Pat. Nos. 4,450,235; 4,302,544; and EP 0134048). The use of *B. subtilis* as an expression host is further described by Palva et al. and others (See, Palva et al., Gene 19:81-87 [1982]; also see Fahnestock and Fischer, J. Bacteriol., 165:796-804 [1986]; and Wang et al., Gene 69:39-47 [1988]).

In certain embodiments, industrial protease producing *Bacillus* strains can serve as parental expression hosts. In some embodiments, use of these strains in the present invention provides further enhancements in efficiency and protease production. Two general types of proteases are typically secreted by *Bacillus* sp., namely neutral (or "metalloproteases") and alkaline (or "serine") proteases. Serine proteases are enzymes which catalyze the hydrolysis of peptide bonds in which there is an essential serine residue at the active site. Serine proteases have molecular weights in the 25,000 to 30,000 range (See, Priest, Bacteriol. Rev., 41:711-753 [1977]). Subtilisin is a serine protease for use in the present invention. A wide variety of *Bacillus* subtilisins have been identified and sequenced, for example, subtilisin 168, subtilisin BPN', subtilisin Carlsberg, subtilisin DY, subtilisin 147 and subtilisin 309 (See e.g., EP 414279 B; WO 89/06279; and Stahl et al., J. Bacteriol., 159:811-818 [1984]). In some embodiments of the present invention, the *Bacillus* host strains produce mutant (e.g., variant) proteases. Numerous references provide examples of variant proteases and reference (See e.g., WO 99/20770; WO 99/20726; WO 99/20769; WO 89/06279; RE 34,606; U.S. Pat. Nos. 4,914,031; 4,980,288; 5,208,158; 5,310,675; 5,336,611; 5,399,283; 5,441,882; 5,482,849; 5,631,217; 5,665,587; 5,700,676; 5,741,694; 5,858,757; 5,880,080; 6,197,567; and 6,218,165).

It is noted here that the present invention is not limited to proteases as the protein of interest. Indeed, the present disclosure encompasses a wide variety of proteins of interest for which increased expression in the Gram positive cell is desired (detailed below).

In other embodiments, a strain for use in aspects of the present invention may have additional genetic alterations in other genes that provide beneficial phenotypes. For example, a *Bacillus* sp. that includes a mutation or deletion in at least one of the following genes, degU, degS, degR and degQ may be employed. In some embodiments, the mutation is in a degU gene, e.g., a degU(Hy)32 mutation. (See, Msadek et al., J. Bacteriol., 172:824-834 [1990]; and Olmos et al., Mol. Gen. Genet., 253:562-567 [1997]). Thus, one example of a parental/genetically altered Gram positive strain that finds use in aspects of the present invention is a *Bacillus subtilis* cell carrying a degU32(Hy) mutation. In a further embodiment, the *Bacillus* host may include a mutation or deletion in scoC4, (See, Caldwell et al., J. Bacteriol., 183:7329-7340 [2001]); oppA or other genes of the opp operon (See, Perego et al., Mol. Microbiol., 5:173-185 [1991]). Indeed, it is contemplated that any mutation in the opp operon that causes the same phenotype as a mutation in the oppA gene will find use in some embodiments of the altered *Bacillus* strain of the present invention. In some embodiments, these mutations occur alone, while in other embodiments, combinations of mutations are present. In some embodiments, an altered *Bacillus* of the invention is obtained from a parental *Bacillus* host strain that already includes a mutation to one or more of the above-mentioned genes. In alternate embodiments, a previously genetically altered *Bacillus* of the invention is further engineered to include mutation of one or more of the above-mentioned genes.

As indicated above, expression of at least one gene of the sin operon is reduced in the genetically altered Gram positive cell as compared to a wildtype and/or parental cell (growm under essentially the same conditions). This reduction of expression can be achieced in any convenient manner, and may be at the level of transcription, mRNA stability, translation, or may be due to the presence of a varation in one or more of the polypeptides produced from the sin operon that reduces its activity (i.e., it is a "functional" reduction of expression based on activity of the polypeptide). As such, no limitation in the type of genetic alteration or the manner through which expression of at least one gene in the sin operon is reduced is intended. For example, in some embodiments the genetic alteration in the Gram positive cell is one that alters one or more of promoters in the sin operon resulting in reduced transcriptional activity. In certain embodiments, the alteration is a silent mutation in the sin operon (e.g., in the sinR gene) that results in reduced levels of mRNA transcript (e.g., as shown in the examples). Alternatively, the genetic alteration in the Gram positive cell can be one that alters a nucleotide in the sin operon resulting in a transcript with reduced stability in the cell. In certain embodiments, more than one genetic alteration that reduces the expression of one or more genes in the sin operon may be present in the genetically altered Gram positive cell.

In certain embodiments, the expression of the one or more genes in the sin operon is reduced in the genetically altered Gram positive cell to about 3% of the level of expression in the wildtype and/or parental cell cultured under essentailly the same culture conditions, including about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 35%, about 40%, about 45%, about 50%, about 55%, about 60%, about 65%, about 70%, about 75%, or about 80%. As such, the range of reduction of expression of the one or more genes in the sin operon can be from about 3% to about 80%, from about 4% to about 75%, from about 5% to about 70%, from about 6% to about 65%, from about 7% to about 60%, from about 8% to about 50%, from about 9% to about 45%, from about 10% to about 40%, from about 11% to about 35%, from about 12% to about 30%, from about 13% to about 25%, from about 14% to about 20%, etc. Any subrange of expression within the ranges set forth above is contemplated.

In certain embodiments, the altered Gram positive bacterial cell has reduced expression of the sinR gene as compared to the expression of these genes in a corresponding unaltered Gram positive bacterial cell grown under essentially the same culture conditions. In particular embodiments, the genetic alteration results in a decrease in the level of an mRNA transcript derived from the sinR gene in the altered Gram positive bacterial cell as compared to a corresponding un-altered Gram positive bacterial cell grown under essentially the same culture conditions.

In certain embodiments, the genetic alteration (or mutation) is one that reduces the expression of the sinR gene in the sin operon. In some of these embodiments, the genetic alteration is in the sinR gene of the sin operon. A sinR gene in a parental Gram positive cell (i.e., prior to being genetically altered as described herein) is a gene that is at least 60% identical to SEQ ID NO:1, including at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identical to SEQ ID NO:1. In certain embociments, the genetic alteration is a deletion of all or a part of the sinR gene. In certain embodiments, the genetic alteration is a silent mulation, where by silent mutation is meant a mutation in the nucleic acid sequence of the coding region of a gene that does not result in an amino acid change in the encoded polypeptide whend translated (a term that is well understood in the art). In certain embodiments, the silent mutation in the variant sequence is at a nucleotide position corresponding to nucleotide 330 of SEQ ID NO: 1. In certain embodiments, the sinR silent mutation is a single nucleotide change from guanine (G) to adenine (A) at nucleotide position 330 of the sense strand of the coding sequence of the wildtype sinR gene (SEQ ID NO:1 shows the sinR wildtype nucleotide sequence; SEQ ID NO:2 shows the SinR amino acid sequence; and SEQ ID NO:3 shows the variant sinR nucleotide sequence having a G330A silent mutation).

As indicated above, many different proteins find use as the protein of interest in the Gram positive cell (i.e., the protein whose expression is increased in the genetically altered cell). The protein of interest can be a homologous protein or a heterologous protein and may be a wildtype protein or a natural or recombinant variant. In certain embodiments, the protein of interest is an enzyme, where in certain instances, the enzyme is selected from a protease, cellulase, pullulanase, amylase, carbohydrase, lipase, isomerase, transferase, kinase, and phosphatase. In certain embodiments, the protein of interest is a protease, where the protese may be a subtilisin, e.g., a subtilisin selected from subtilisin 168, subtilisin BPN', subtilisin Carlsberg, subtilisin DY, subtilisin 147, subtilisin 309, and variants thereof. In certain embododimetns, the protein of interest is a fluorescent protein, e.g., green fluorescent protein (GFP).

In certain embodiments, the method further comprisies recovering the protein of interest. Because the level of expression/production of the protein of interest is increased in the genetically altered Gram positive cell (as comparet to q wildtype or parental cell), the amount of the protein of interest recovered is increases as compared to the corresponding wildtype and/or parental cell cultured under essentiall the same culture conditions (and at the same scale). There are various assays known to those of ordinary skill in the art for detecting and measuring the expression level/production of intracellularly and extracellularly expressed polypeptides. Such assays will be determined by the user of the present invention and may depend on the identity and/or activity (e.g., enzymatic activity) of the protein of interest. For example, for proteases, there are assays based on the release of acid-soluble peptides from casein or hemoglobin measured as absorbance at 280 nm or colorimetrically using the Folin method (See e.g., Bergmeyer et al., "Methods of Enzymatic Analysis" vol. 5, *Peptidases, Proteinases and their Inhibitors*, Verlag Chemie, Weinheim [1984]). Other assays involve the solubilization of chromogenic substrates (See e.g., Ward, "Proteinases," in Fogarty (ed.)., *Microbial Enzymes and Biotechnology*, Applied Science, London, [1983], pp 251-317). Other examples of assays include succinyl-Ala-Ala-Pro-Phe-para nitroanilide assay (SAAP-FpNA) and the 2,4,6-trinitrobenzene sulfonate sodium salt assay (TNBS assay). Numerous additional references known to those in the art provide suitable methods (See e.g., Wells et al., Nucleic Acids Res. 11:7911-7925 [1983]; Christianson et al., Anal. Biochem., 223:119-129 [1994]; and Hsia et al., Anal Biochem., 242:221-227 [1999]).

Also as indicated above, means for determining the levels of secretion of a protein of interest in a host cell and detecting expressed proteins include the use of immunoassays with either polyclonal or monoclonal antibodies specific for the protein of interest. Examples include enzyme-linked immunosorbent assay (ELISA), radioimmunoassay (RIA), fluorescence immunoassay (FIA), and fluorescent activated cell sorting (FACS). However, other methods are known to those in the art and find use in assessing the protein of interest (See e.g., Hampton et al., *Serological Methods, A Laboratory Manual*, APS Press, St. Paul, Minn. [1990]; and Maddox et al., J. Exp. Med., 158:1211 [1983]). As known in the art, the altered *Bacillus* cells produced using the present invention are maintained and grown under conditions suitable for the expression and recovery of a polypeptide of interest from cell culture (See e.g., Hardwood and Cutting (eds.) *Molecular Biological Methods for Bacillus*, John Wiley & Sons [1990]). It is further noted that a genetically altered cell as described herein may express more than one protein of interest, including two or more, three or more, four or more, five or more, six or more, seven or more, eight or more, nine or more, ten or more, etc. In some embodiments, increased expression of proteins in the bacterial secretome is desired, which includes numerous different proteins that are secretred from the cell.

Aspects of the present invention include a method for obtaining an altered Gram positive bacterial cell with improved protein production capability. In general, the method includes genetically altering a parental Gram positive cell to result in a genetically altered strain in which the expression of one or more gene in the sin operon is reduced (as defined above).

In certain embodiments, the method includes introducing a polynucleotide sequence into a parental Gram positive bacterial cell that, when integrated into the chromosome or sustained as an episomal genetic element, results in a genetically altered Gram positive cell in which the expression level of one or more genes in the sin operon is reduced.

Various methods are known for the transformation of *Bacillus* species to alter the chromosome of, or to maintain an episomal genetic element in, *Bacillus* using polynucldotide vectors (e.g., plasmid constructs) are well known. Suitable methods for introducing polynucleotide sequences into *Bacillus* cells are found in, e.g., Ferrari et al., "Genetics," in Harwood et al. (ed.), *Bacillus*, Plenum Publishing Corp. [1989], pages 57-72; See also, Saunders et al., J. Bacteriol., 157:718-726 [1984]; Hoch et al., J. Bacteriol., 93:1925-1937 [1967]; Mann et al., Current Microbiol., 13:131-135 [1986]; and Holubova, Folia Microbiol., 30:97 [1985]; for *B. subtilis*, Chang et al., Mol. Gen. Genet., 168:11-115 [1979]; for *B. megaterium*, Vorobjeva et al., FEMS Microbiol. Lett., 7:261-263 [1980]; for *B amyloliquefaciens*, Smith et al., Appl. Env. Microbiol., 51:634 (1986); for *B. thuringiensis*, Fisher et al., Arch. Microbiol., 139:213-217 [1981]; and for *B. sphaericus*, McDonald, J. Gen. Microbiol., 130:203 [1984]. Indeed, such methods as transformation including protoplast transformation and congression, transduction, and protoplast fusion are known and suited for use in the present invention. Methods of transformation are particularly to introduce a DNA construct provided by the present invention into a host cell In addition, introduction of a DNA construct into the host cell includes physical and chemical methods known in the art to introduce DNA into a host cell without insertion of the targeting DNA construct into a plasmid or vector. Such methods include, but are not limited to calcium chloride precipitation, electroporation, naked DNA, liposomes and the like. In additional embodiments, DNA constructs can be co-transformed with a plasmid, without being inserted into the plasmid.

In embodiments in which selectable marker genes are used to select for stble transformants, it may be desireable to delete the selective marker from the genetically altered Gram positive strain using any convenient method, with numerous methods being known in the art (See, Stahl et al., J. Bacteriol., 158:411-418 [1984]; and Palmeros et al., Gene 247:255-264 [2000]).

In some embodiments, two or more DNA constructs (i.e., DNA constructs that each are designed to genetically alter a host cell) are introduced into a parental Gram positive cell, resulting in the introduction of two or more genetic alterations in the cell, e.g., alterations at two or more chromosomal regions. In some embodiments, these regions are contiguous, (e.g., two regions within the sin operon or within the sin operon and an adjacent gene or operon), while in other embodiments, the regions are separated. In some embodiments, one or more of the genetic alterations are by addition of an episomal genetic element.

In some embodiments, host cells are transformed with one or more DNA constructs according to the present invention to produce an altered *Bacillus* strain wherein two or more genes have been inactivated in the host cell. In some embodiments, two or more genes are deleted from the host cell chromosome. In alternative embodiments, two or more genes are inactivated by insertion of a DNA construct. In some embodiments, the inactivated genes are contiguous (whether inactivated by deletion and/or insertion), while in other embodiments, they are not contiguous genes.

Once a genetically altered host cell is produced, it can be cultured under conditions such that the protein of interest is expressed, where in certain embodiments the protein of interest is recovered.

Aspects of the present invention include an altered Gram positive bacterial cell, where the altered Gram positive bacterial cell comprises at least one genetic alteration that reduces expression of one or more genes in the sin operon as compared to a corresponding unaltered Gram positive bacterial cell grown under essentially the same culture conditions. In some embodiments, the genetically altered Gram positive cell is produced as described above. As further noted above, the altered Gram positive bacterial cell can be a *Bacillus* sp. strain, e.g., a *B. licheniformis, B. lentus, B. subtilis, B. amyloliquefaciens, B. brevis, B. stearothermophilus, B. alkalophilus, B. coagulans, B. circulans, B. pumilus, B. lautus, B. clausii, B. megaterium*, or *B. thuringiensis* strain. In certain embodiments, the *Bacillus* sp. strain is a *B. subtilis* strain. In some aspects, the altered Gram positive bacterial cell further comprises an additional mutation that improves a phenotype of the cell, e.g., a mutation in a gene selected from the group consisting of degU, degQ, degS, scoC4, and oppA. In certain embodiments, the mutation is degU(Hy)32.

In certain embodiments, expression of at least one gene of the sin operon is reduced in the genetically altered Gram positive cell as compared to a wildtype and/or parental cell (grown under essentially the same conditions). This reduction of expression can be achieved in any convenient manner, and may be at the level of transcription, mRNA stability, translation, or may be due to the presence of a varation in one or more of the polypeptides produced from the sin operon that reduces its activity (i.e., it is a "functional" reduction of expression based on activity of the polypeptide). As such, no limitation in the type of genetic alteration or the manner through which expression of at least one gene in the sin operon is reduced is intended. For example, in some embodiments the genetic alteration in the Gram positive cell is one that alters one or more of promoters in the sin operon resulting in reduced transcriptional activity. In certain embodiments, the alteration is a silent mutation in the sin operon that results in reduced levels of mRNA transcript (e.g., as shown in the examples). Alternatively, the genetic alteration in the Gram positive cell can be one that alters a nucleotide in the sin operon resulting in a transcript with reduced stability in the cell. In certain embodiments, more than one genetic alteration that reduces the expression of one or more genes in the sin operon may be present in the genetically altered Gram positive cell. In certain embodiments, the genetic alteration results in a decrease in the level of an mRNA transcript derived from the sin operon in the altered Gram positive bacterial cell as compared to a corresponding unaltered Gram positive bacterial cell grown under essentially the same culture conditions.

In some embodiments, the present invention includes a DNA construct comprising an incoming sequence that, when stably incorporated into the host cell, genetically alters the cell such that expression of one or more genes in the sin operon is reduced (as described in detail above). In some embodiments, the DNA construct is assembled in vitro, followed by direct cloning of the construct into a competent Gram positive (e.g., *Bacillus*) host such that the DNA construct becomes integrated into the host cell chromosome. For example, PCR fusion and/or ligation can be employed to assemble a DNA construct in vitro. In some embodiments, the DNA construct is a non-plasmid construct, while in other embodiments it is incorporated into a vector (e.g., a plasmid). In some embodiments, circular plasmids are used. In embodiments, circular plasmids are designed to use an appropriate restriction enzyme (i.e., one that does not disrupt the DNA construct). Thus, linear plasmids find use in the present invention. However, other methods are suitable for use in the present invention, as known to those in the art (See e.g., Perego, "Integrational Vectors for Genetic Manipulation in *Bacillus subtilis*," in (Sonenshein et al. (eds.), *Bacillus subtilis and Other Gram-Positive Bacteria*, American Society for Microbiology, Washington, D.C. [1993]).

In certain embodiments, the DNA targeting vector is designed to delete (or allow for the deletion of) all or part of the sinR gene. For example, the DNA targeting vector can include elements that allow for removal of all or part of the sinR gene (e.g., usong a cre-lox system as is known in the art). In certain embodiments, the incoming sequence of a DNA targeting vector incudes a polynucleotide comprising a variant sequence derived from the sinR gene. In some of these embodiments, the variant sequence is at least about 15 nucleotides in length, is at least 60% identical to all or a part of SEQ ID NO:1, and has at least one mutation at a nucleotide position in the sinR gene that leads to reduced expression of a gene in the sin operon when the mutation is present in the endogenous sinR gene of a Gram positive bacterial cell. The variant sequence can be at least about 20 nucleotides, about 30 nucleotides, about 40 nucleotides, about 50 nucleotides, about 60 nucleotides, about 80 nucleotides, about 90 nucleotides, about 100 nucleotides, about 200 nucleotides, about 300 nucleotides, about 400 nucleotides, about 500 nucleotides, about 600 nucleotides, about 700 nucleotides, about 800 nucleotides, about 900 nucleotides, about 1000 nucleotides, about 1100 nucleotides, about 1200 nucleotides, about 1300 nucleotides, about 1400 or more nucleotides. As further noted above, the variant sequence can be at least 60% identical to SEQ ID NO:1, including at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% identical to SEQ ID NO:1. In certain embodiments, the genetic alteration in the variant sequence is a silent mulation, where by silent mutation is meant a mutation in the variant sequence of the coding region of the sinR gene that does not result in an amino acid change in the encoded SinR polypeptide when translated (a term that is well understood in the art). In certain embodiments, the silent mutation in the variant sequence is at a nucleotide position corresponding to nucleotide 330 of SEQ ID NO: 1. In certain embodiments, the sinR silent mutation is a single nucleotide change from guanine (G) to adenine (A) at nucleotide position 330 of the sense strand of the coding sequence of the wildtype sinR gene (SEQ ID NO:1 shows the sinR wildtype nucleotide sequence; SEQ ID NO:2 shows the SinR amino acid sequence; and SEQ ID NO:3 shows the variant sinR nucleotide sequence having a G330A silent mutation).

Aspects of the present invention include a vector comprising the polynucleotide sequence as described above. In certain embodiments, the vector is a targeting vector designed to introduce the at least one mutation in the polynucleotide sequence into the corresponding location in the sin operon of a Gram positive bacterial cell by homologous recombination when transformed into the Gram positive bacterial cell. In some embodiments, the incoming sequence/vector includes a selective marker. In some embodiment, the selective marker located between two loxP sites (See, Kuhn and Torres, Meth. Mol. Biol., 180:175-204 [2002]), and the antimicrobial gene is then deleted by the action of Cre protein.

Aspects of the present invention include a method for enhancing expression of a protein of interest in a Gram positive bacterial cell that includes transforming a parental Gram positive bacterial cell with the DNA construct or vector described above (i.e., one that includes an incoming sequence that, when stably incorporated into the host cell, genetically alters the cell such that expression of one or more genes in the sin operon is reduced, e.g., one that includes a mutation in the sinR gene as set forth above), allowing homologous recombination of the vector and the corresponding region in the sin operon of the parental Gram positive bacterial cell to produce an altered Gram positive bacterial cell; and growing the altered Gram positive bacterial cell under conditions suitable for the expression of the protein of interest, where the production of the protein of interest is increased in the altered Gram positive bacterial cell as compared to the Gram positive bacterial cell prior to the transformation in step. Examples of the Gram positive strains, mutations and other features that find use in this aspect of the invention are described in detail above.

Whether the DNA construct is incorporated into a vector or used without the presence of plasmid DNA, it is used to transform microorganisms. It is contemplated that any suitable method for transformation will find use with the present invention. In embodiments, at least one copy of the DNA construct is integrated into the host *Bacillus* chromosome. In some embodiments, one or more DNA constructs of the invention are used to transform host cells.

The manner and method of carrying out the present invention may be more fully understood by those of skill in the art by reference to the following examples, which examples are not intended in any manner to limit the scope of the present invention or of the claims directed thereto.

EXPERIMENTAL

The following Examples are provided in order to demonstrate and further illustrate certain embodiments and aspects of the present invention and are not to be construed as limiting the scope thereof.

In the experimental disclosure which follows, certain of the following abbreviations apply: ° C. (degrees Centigrade); rpm (revolutions per minute); µg (micrograms); mg (milligrams); µl (microliters); ml (milliliters); mM (millimolar); µM (micromolar); sec (seconds); min(s) (minute/minutes); hr(s) (hour/hours); $OD_{280}$ (optical density at 280 nm); $OD_{600}$ (optical density at 600 nm); PCR (polymerase chain reaction); RT-PCR (reverse transcription PCR); SDS (sodium dodecyl sulfate); Abs (absorbance).

Example 1

Increased Protein Expression in Bacillus by Mutation in the sinR Gene

A. Mutation in the sinR Gene in Bacillus subtilis

A silent mutation was introduced into a parental Bacillus subtilis strain (oppA::tetR, ΔaprE, ΔnprE, degUHy32, referred to herein as "the parental strain") in the sinR gene using the marker-less gene replacement method described by Janes and Stibitz (Infection and Immunity, 74(3):1949, 2006). The sinR silent mutation is a single nucleotide change from guanine (G) to adenine (A) at nucleotide position 330 of the sense strand of the coding sequence of wildtype sinR (SEQ ID NO:1 shows the wildtype sequence; SEQ ID NO:2 shows the SinR amino acid sequence and SEQ ID NO:3 shows the G330A silent mutation) (a silent mutation is a mutation that changes the nucleic acid sequence of a site in the coding region of a gene but does not change the amino acid sequence of the encoded polypeptide).

The genomic region containing the sinR G>A synonymous mutation at position 330 of the sinR gene was amplified from the strain FCM102 using the following primers:

```
EcoRI sinR FW:
                                    SEQ ID NO: 4
5'-caggaattcctgacgtctcaaatatgtgactattg-3'

BamHI sinR RV:
                                    SEQ ID NO: 5
5'-ctcggatccgagaaattgaaagaaagacaaaagc-3'
```

The amplified fragment was cloned into the pKSV7-I-Sce-Km vector (FIG. 1); this plasmid is derived from pKSV7 (Smith K. and Youngman P. Biochimie (1992) 74, 705-711), the chloramphenicol resistant marker was replaced with the kanamycin resistant marker and the I-Sce restriction site was added to the polylinker of the plasmid. The method of Janes and Stibitz was used to introduce the single nucleotide polymorphism into the sinR gene. The resultant strain CB15-14 sinR is sometimes referred to herein as "the sinR mutated strain", "sinR*", "the mutant strain", or equivalents thereof. The non-mutated strain (CB15-14) is sometimes referred to herein as "the parental strain" or equivalents thereof.

B. Deletion of the sinR Gene in Bacillus subtilis Strain

Figure 2:
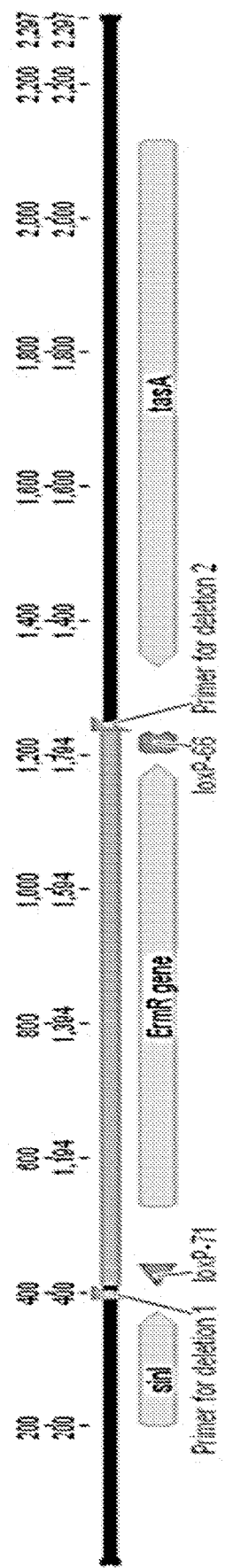
FIG. 2 shows a schematic of the genetic map of the sinR deletion (ΔsinR).

The sinR deleted strain derived from B. subtilis 168 (BKE24610) was obtained from the Bacillus Genetic Stock Center (bgsc.org/). Chromosomal DNA of BKE24610 was extracted and transformed in a B. subtilis "parental strain". The deletion was confirmed by PCR and sequencing of the sinR locus. The resultant strain is denoted by B. subtilis AsinR or sinR::ermR. FIG. 2 shows a genetic map of the sinR deletion. The ORF of the sinR gene was deleted and replaced with an erythromycin resistance cassette flanked by loxP sites (lox 71 and lox 66) for easy removal of the erythromycin resistance marker using a plasmid encoded cre recombinase. The ORFs of the flanking sinI and tasA genes remained unchanged from the knockout of the sinR gene.

C. Protease Expression in sinR Mutated or sinR Deleted Bacillus Strains

Figure 3A:
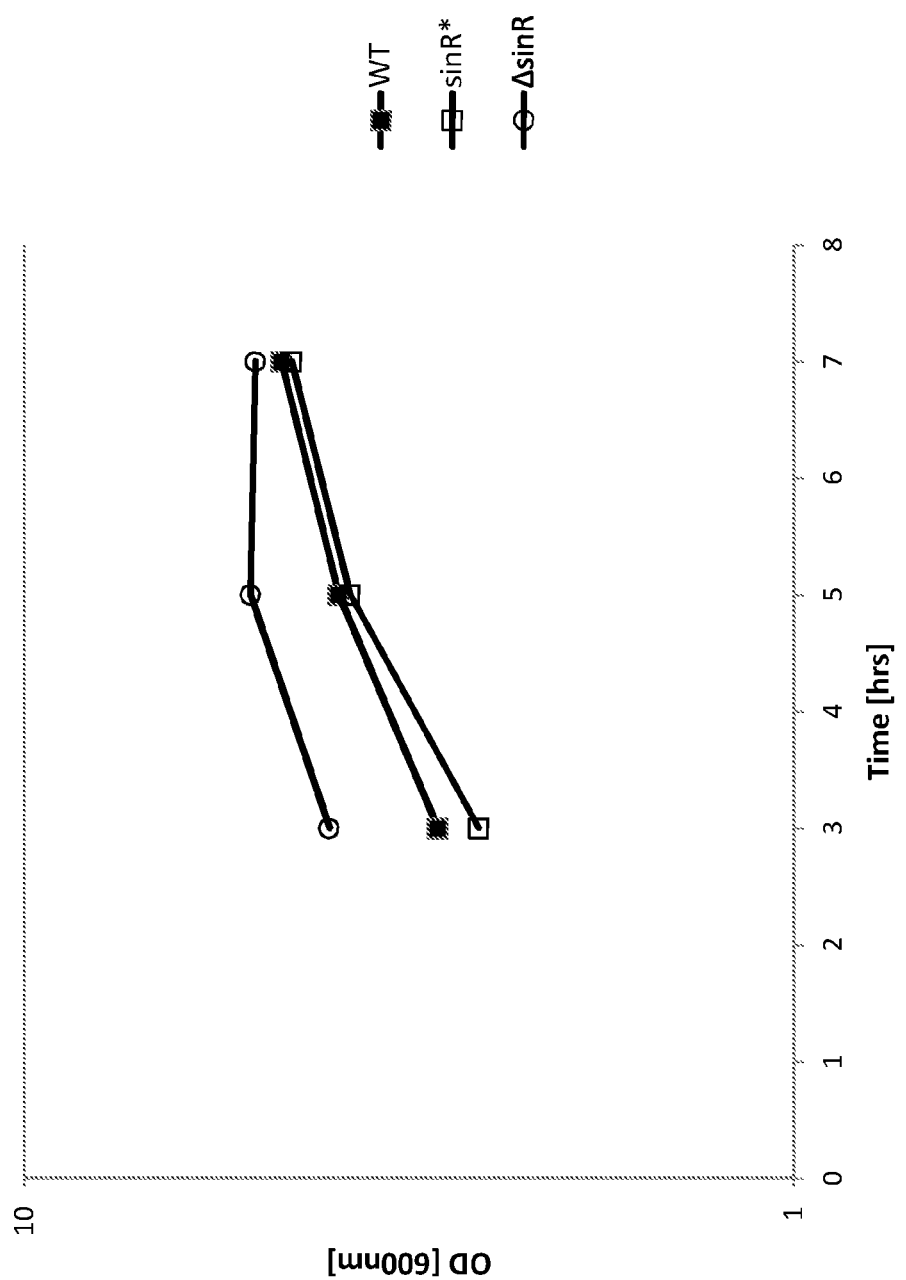
FIG. 3A shows a cell density graph of *Bacillus subtilis* cells expressing FNA protease. WT is an "unaltered" (parent) *Bacillus subtilis* (control) cell, sinR* is an "altered" (daughter) *Bacillus subtilis* cell comprising a silent mutation corresponding to nucleotide 330 of the sinR gene and ΔsinR is an "altered (daughter) *Bacillus subtilis* cell comprising a deleted sinRgene (e.g., see, FIG. 2).

To test the effect of the sinR mutation and deletion on expression of FNA protease (subtilisin BPN' containing the Y217L substitution; SEQ ID NO:6), the construct nprE::PrrnE2/3-FNA-catR (expresses FNA from the rrnE 2/3 ribosomal promoters of Bacillus subtilis and includes a chloramphenico acetyltransferase resistance (catR) marker gene) was introduced in the nprE locus of the parental strain and the sinR* and ΔsinR strains. The transformants were selected on Luria Agar plates containing 5 ppm chloramphenicol. The wildtype/parent strain and mutant strains (sinR* and sinR::ermR) were grown overnight in LB medium at 30° C. Ten microliters of pre-culture was used to inoculate 165 microliters of Brain Heart Infusion (BHI) medium. The strains were grown at 37° C. and samples were taken from 3 hours of growth. Cell densities of whole broth diluted 20× were measured at 600 nm at hourly intervals using a SpectraMax spectrophotometer (Molecular Devices, Downington, Pa., USA). The absorbance at 600 nm was plotted as a function of time and the results are shown in FIG. 3A. FIG. 3A shows that the cell growth of the FNA expressing parental strain (WT) and sinR* and ΔsinR strains was equivalent at 7 hours of growth.

Figure 3B:
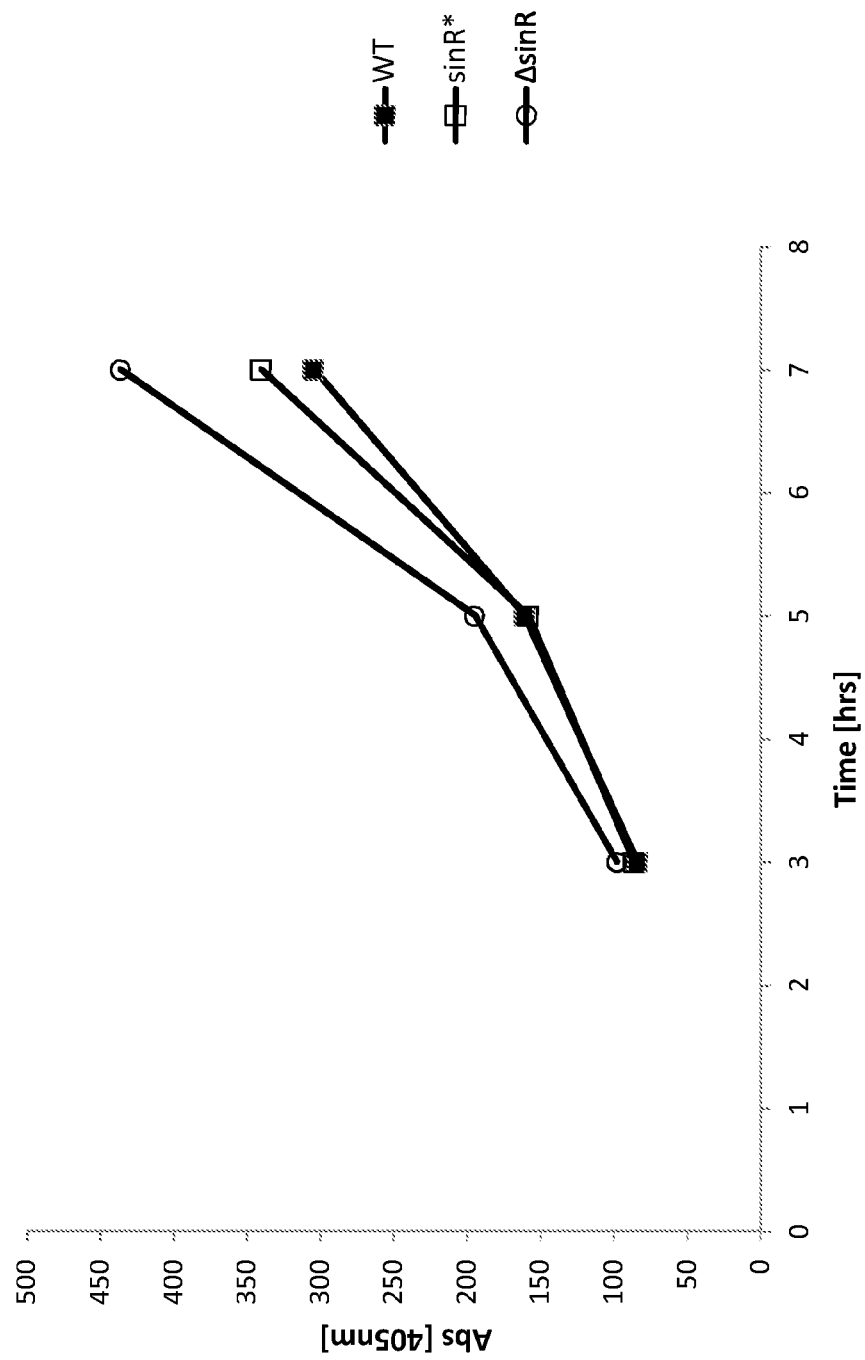
FIG. 3B shows a graph of FNA protease expression in the WT and altered *Bacillus subtilis* cells presented in FIG. 3A. WT is an "unaltered" (parent) *Bacillus subtilis* (control) cell, sinR* is an "altered" (daughter) *Bacillus subtilis* cell comprising a silent mutation corresponding to nucleotide 330 of the sinR gene and ΔsinR is an "altered (daughter) *Bacillus subtilis* cell comprising a deleted sinR gene.

Protease expression was monitored using N-suc-AAPF-pNA substrate (from Sigma Chemical Co.) as described in WO 2010/144283. Briefly, whole broth was diluted 40× in the assay buffer (100 mM Tris, 0.005% Tween 80, pH 8.6) and 10 µl of the diluted samples were arrayed in microtiter plates. The AAPF stock was diluted and the assay buffer (100× dilution of 100 mg/ml AAPF stock in DMSO) and 190 µl of this solution were added to the microtiter plates and the absorbance of the solution was measured at 405 nm using a SpectraMax spectrophotometer (Molecular Devices, Downington, Pa., USA). The absorbance at 405 nm was plotted as a function of time and the results are shown in FIG. 3B. As shown in FIG. 3B, FNA production is increased in the mutant strains (sinR* and ΔsinR) compared to the wildtype strain (WT).

D. Amylase Expression in sinR Mutated or sinR Deleted Bacillus Strains

Figure 4A:
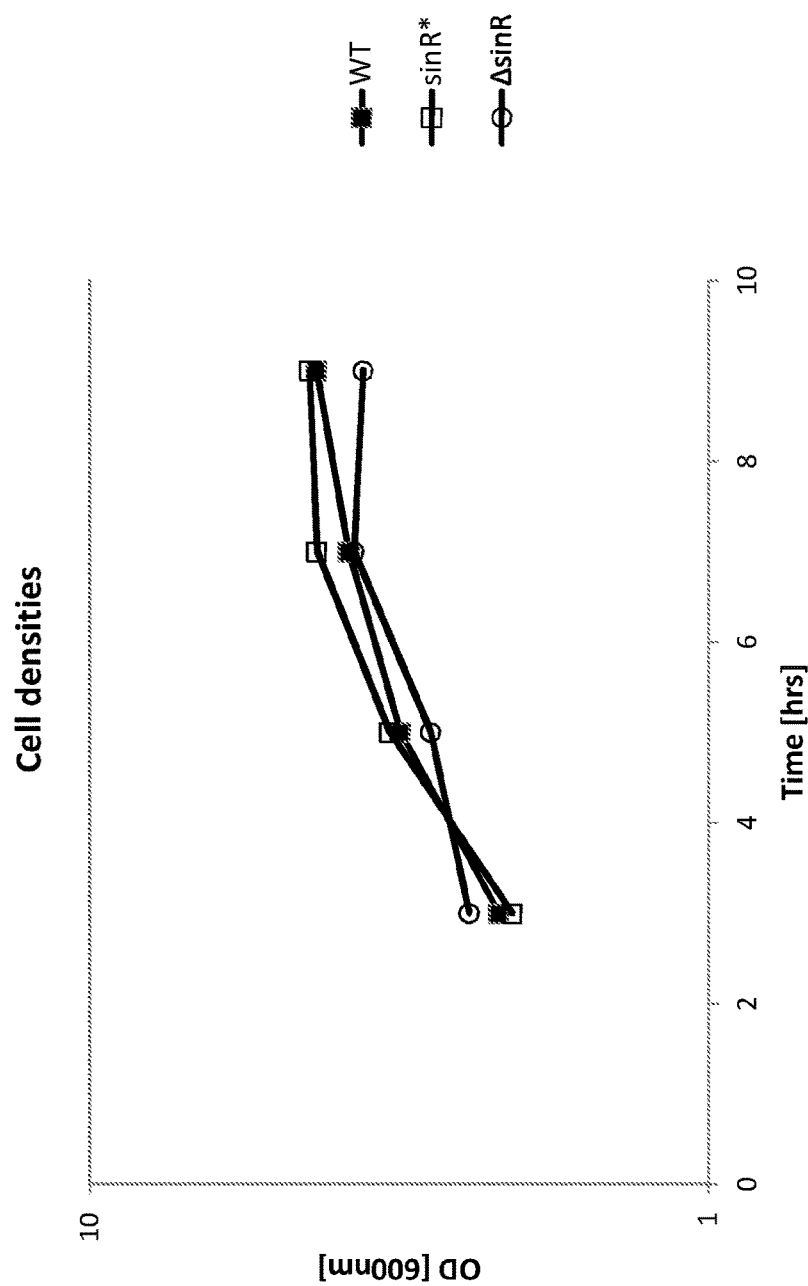
FIG. 4A shows a graph of cell densities of AmyE expression in the WT and altered *Bacillus subtilis* cells. WT is an "unaltered" (parent) *Bacillus subtilis* (control) cell, sinR* is an "altered" (daughter) *Bacillus subtilis* cell comprising a silent mutation corresponding to nucleotide 330 of the sinR gene and ΔsinR is an "altered (daughter) *Bacillus subtilis* cell comprising a deleted sinR gene.

To determine the effect of the sinR mutation and deletion on amylase expression (SEQ ID NO:7), the construct PaprE-amyE catR was introduced in B. subtilis parental strains deleted for the sinR gene or containing the sinR mutation. Transformants were selected on LA plates containing 5 ppm of chloramphenicol. The WT strain (CB15-14) and mutant strains (sinR* and sinR::ermR) were grown overnight in Luria Broth medium. Ten microliters of preculture was used to inoculate 165 microliters of Tryptic Soy Broth (Bacto Tryptone 17 g/L, Bacto Soytone 3 g/L, Glucose 2.5 g/L, Sodium Chloride 5 g/L, Dipotassium hydrogen phosphate 2.5 g/L pH7.3) and strains were grown at 30° C. to test the expression of the amyE amylase. Cell densities were measured at 600 nm at hourly intervals using a SpectraMax spectrophotometer (Molecular Devices, Downington, Pa., USA). The absorbance at 600 nm was plotted as a function of time and the results are shown in FIG. 4A. FIG. 4A shows that cell growth of the AmyE expressing parental strain and the AmyE expressing sinR* and ΔsinR strains is equivalent, indicating that the mutation or deletion of the sinR gene in the *B. subtilis* strain does not affect the cell growth.

Figure 4B:
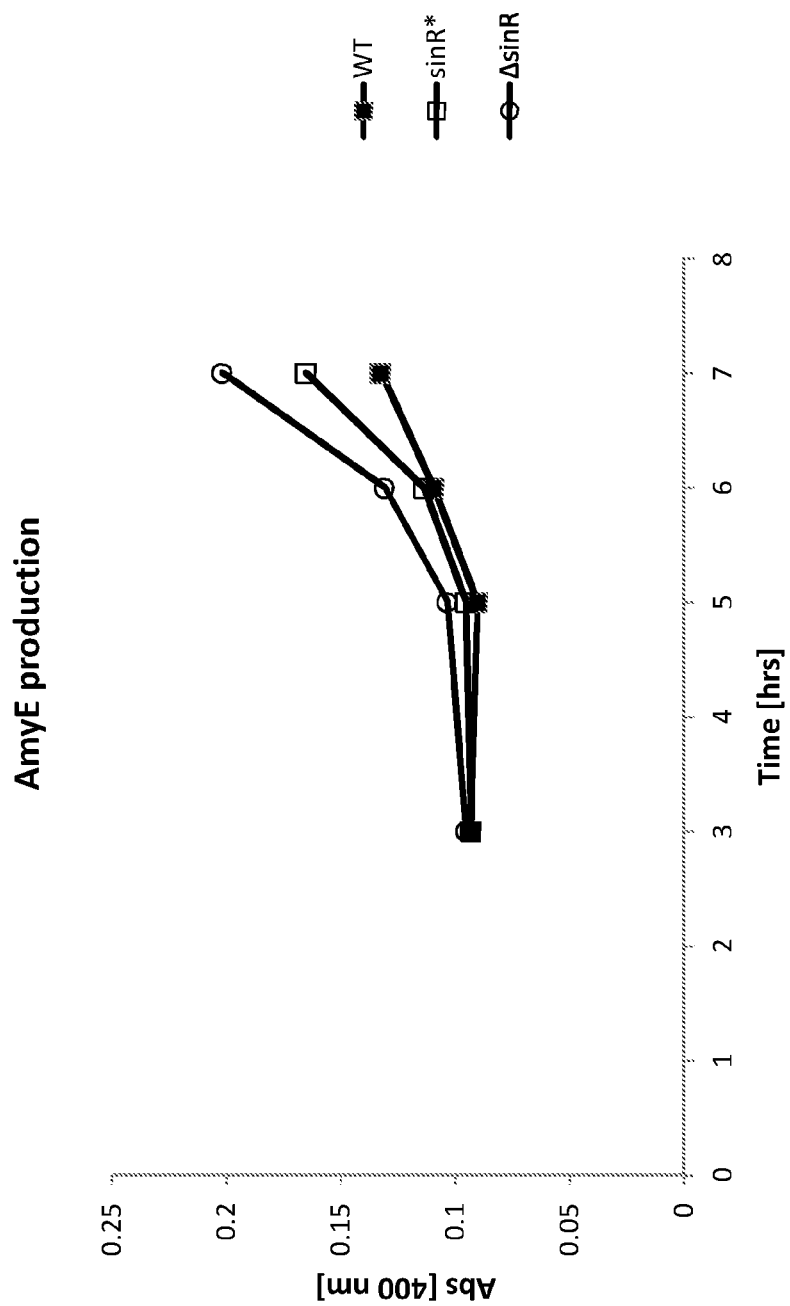
FIG. 4B shows a graph of AmyE amylase expression in the WT and altered *Bacillus subtilis* cells. WT is an "unaltered" (parent) *Bacillus subtilis* (control) cell, sinR* is an "altered" (daughter) *Bacillus subtilis* cell comprising a silent mutation corresponding to nucleotide 330 of the sinR gene and ΔsinR is an "altered (daughter) *Bacillus subtilis* cell comprising a deleted sinR gene.

AmyE amylase activity of whole broth was measured using the Ceralpha reagent (Megazyme, Wicklow, Ireland.). The Ceralpha reagent mix from the Ceralpha HR kit was initially dissolved in 10 ml of MilliQ water followed by the addition of 30 ml of 50 mM malate buffer, pH 5.6. The culture supernatants were diluted 40× in MilliQ water and 5 μl of diluted sample was added to 55 μL of diluted working substrate solution. The MTP plate was incubated for 4 minutes at room temperature after shaking. The reaction was quenched by adding 70 μl of 200 mM borate buffer pH 10.2 (stop solution). The absorbance of the solution was measured at 400 nm using a SpectraMax spectrophotometer (Molecular Devices, Downington, Pa., USA). The absorbance at 400 nm was plotted as a function of time and the results are shown in FIG. 4B. The graph in FIG. 4B shows increased AmyE expression in sinR* and ΔsinR strains compared to the wildtype (WT) strain.

Figure 5A:
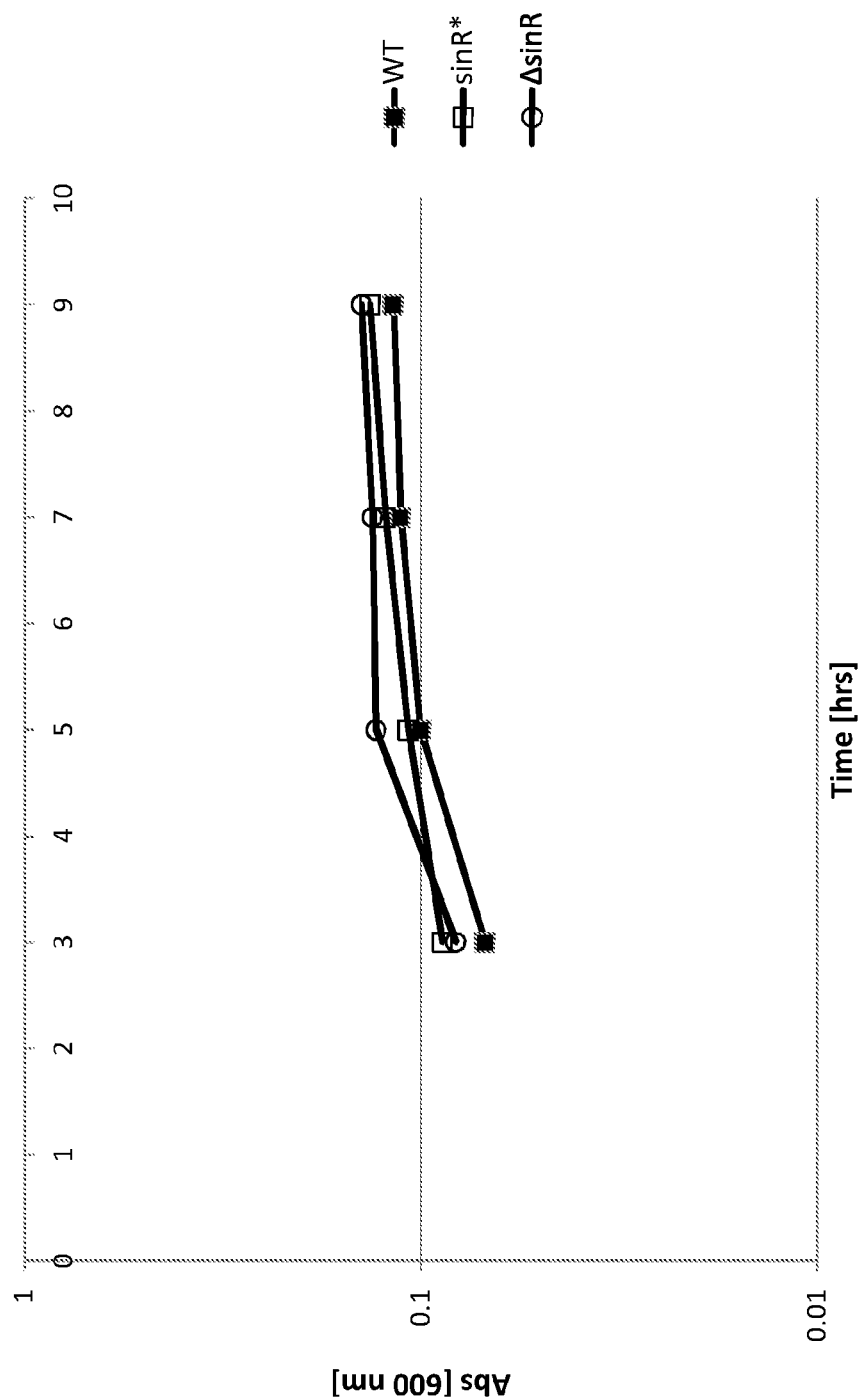
FIG. 5A shows a graph of cell densities of WT and altered *Bacillus subtilis* cells. WT is an "unaltered" (parent) *Bacillus subtilis* (control) cell, sinR* is an "altered" (daughter) *Bacillus subtilis* cell comprising a silent mutation corresponding to nucleotide 330 of the sinR gene and ΔsinR is an "altered (daughter) *Bacillus subtilis* cell comprising a deleted sinR gene.

E. Endogenous Gene Expression in sinR Mutated or sinR Deleted *Bacillus* Strains To test the effect of sinR mutation or sinR deletion on endogenous gene expression, the sinR mutation or sinR deletion were introduced in the parental strain as described previously. The activity of apectate lyase (SEQ ID NO:8) protein was assessed in shake flasks in BHI medium. The WT parental strain and mutant strains (sinR* and sinR::ermR) were grown overnight in LB medium at 30° C. One milliliter of pre-culture was used to inoculate 20 ml of BHI medium in shake flasks. The strains were grown at 37° C. to test expression of the pectate lyase enzyme. Cell densities were measured at 600 nm at hourly intervals using a SpectraMax spectrophotometer (Molecular Devices, Downington, Pa., USA). The absorbance at 600 nm was plotted as a function of time and the results are shown in FIG. 5A. FIG. 5A shows that cell growth of the parental strain and the sinR* and ΔsinR strains is equivalent, indicating that the mutation or deletion of the sinR gene in the strain does not affect the cell growth.

Figure 5B:
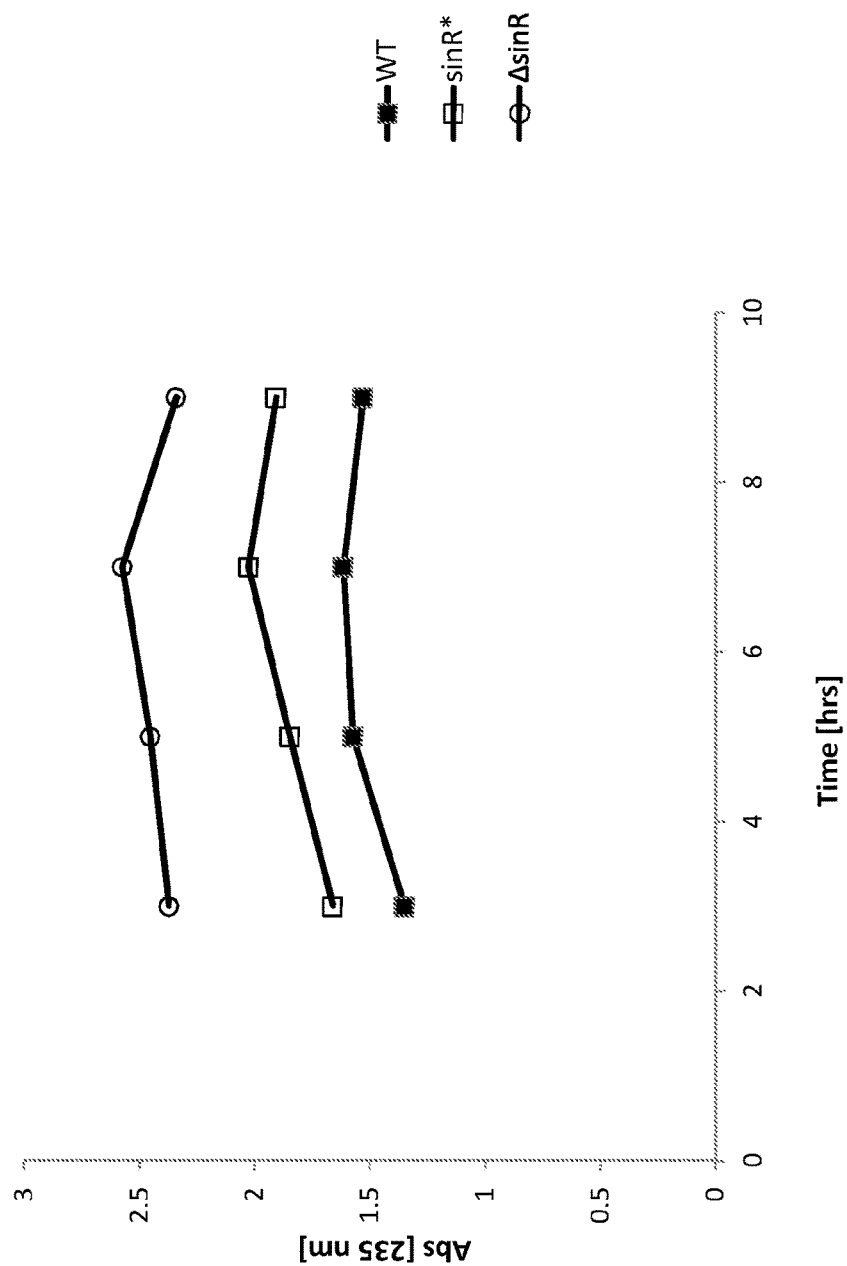
FIG. 5B shows a graph of pelC expression in WT and altered *Bacillus subtilis* cells. WT is an "unaltered" (parent) *Bacillus subtilis* (control) cell, sinR* is an "altered" (daughter) *Bacillus subtilis* cell comprising a silent mutation corresponding to nucleotide 330 of the sinR gene and ΔsinR is an "altered (daughter) *Bacillus subtilis* cell comprising a deleted sinR gene.

Pectate lyase activity was monitored using polygalacturonic acid potassium salt (Sigma P0853) substrate. The substrate solution was prepared by dissolving 0.6% w/v polygalacturonic acid potassium salt in Tris Assay Buffer (0.1M TRIS, 1 mM $CaCl_2$, 1% PEG-8000 pH 7.73). One hundred microliters of the substrate solution was added to 20 microliters of sample supernatants. The reaction was incubated at 37° C. for 10 minutes. Following incubation, 200 microliters of the stop solution (0.05 M Phosphoric Acid) was added to the samples and the absorbance of the solution was measured at 235 nm using a quartz 96 well microtiter plate. The absorbance at 235 nm was plotted as a function of time and the results are shown in FIG. 5B. The graph in FIG. 5B shows increased pectate lyase expression in sinR* and ΔsinR strains compared to the wildtype (WT) strain.

Although the foregoing compositions and methods have been described in some detail by way of illustration and example for purposes of clarity of understanding, it is readily apparent to those of ordinary skill in the art in light of the teachings herein that certain changes and modifications may be made thereto without departing from the spirit or scope of the appended claims.

Accordingly, the preceding merely illustrates the principles of the present compositions and methods. It will be appreciated that those skilled in the art will be able to devise various arrangements which, although not explicitly described or shown herein, embody the principles of the present compositions and methods and are included within its spirit and scope. Furthermore, all examples and conditional language recited herein are principally intended to aid the reader in understanding the principles of the present compositions and methods and the concepts contributed by the inventors to furthering the art, and are to be construed as being without limitation to such specifically recited examples and conditions. Moreover, all statements herein reciting principles, aspects, and embodiments of the present compositions and methods as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present compositions and methods, therefore, is not intended to be limited to the exemplary embodiments shown and described herein.

```
sinR wildtype coding sequence, sense strand (with stop codon)
                                                    SEQ ID NO: 1
TTGATTGGCCAGCGTATTAAACAATACCGTAAAGAAAAAGGCTACTCACTATCAGAACTAGC

TGAAAAAGCTGGGGTAGCGAAGTCTTATTTAAGCTCAATAGAACGAAATCTACAAACGAACC

CCTCCATTCAATTTCTCGAAAAAGTCTCCGCTGTTCTGGACGTCTCGGTTCATACTTTGCTC

GATGAGAAACATGAAACCGAATACGATGGTCAATTAGATAGTGAATGGGAGAAATTGGTTCG

CGATGCGATGACATCCGGGGTATCGAAAAAACAATTTCGTGAATTTTTAGATTATCAAAAAT

GGAGAAAATCCCAAAAAGAGGAGtag sinR protein sequence
                                                    SEQ ID NO: 2
MIGQRIKQYRKEKGYSLSELAEKAGVAKSYLSSIERNLQTNPSIQFLEKVSAVLDVSVHTLL

DEKHETEYDGQLDSEWEKLVRDAMTSGVSKKQFREFLDYQKWRKSQKEE sinR mutant caging sequence, sense strand
(with G330A silent mutation in bold underline; with stop codon)
                                                    SEQ ID NO: 3
TTGATTGGCCAGCGTATTAAACAATACCGTAAAGAAAAAGGCTACTCACTATCAG

AACTAGCTGAAAAAGCTGGGGTAGCGAAGTCTTATTTAAGCTCAATAGAACGAAA
```

-continued

TCTACAAACGAACCCCTCCATTCAATTTCTCGAAAAAGTCTCCGCTGTTCTGGACG

TCTCGGTTCATACTTTGCTCGATGAGAAACATGAAACCGAATACGATGGTCAATT

AGATAGTGAATGGGAGAAATTGGTTCGCGATGCGATGACATCCGGGGTATCGAA

AAAACAATTTCGTGAATTTTTAGATTATCAAAAATGGAGAAAATCCCAAAAAGAA

GAGtag

Forward primer for amplification of the sinR gene
SEQ ID NO: 4
5'-caggaattcctgacgtctcaaatatgtgactattg-3'

Reverse primer for amplification of the sinR gene
SEQ ID NO: 5
5'-ctcggatccgagaaattgaaagaaagacaaaagc-3'

FNA protein sequence (with pro-domain)
SEQ ID NO: 6
AQSVPYGVSQIKAPALHSQGYTGSNVKVAVIDSGIDSSHPDLKVAGGASMVPSETNPFQDNN

SHGTHVAGTVAALNNSIGVLGVAPSASLYAVKVLGADGSGQYSWIINGIEWAIANNMDVINM

SLGGPSGSAALKAAVDKAVASGVVVVAAAGNEGTSGSSSTVGYPGKYPSVIAVGAVDSSNQR

ASFSSVGPELDVMAPGVSIQSTLPGNKYGALNGTSMASPHVAGAAALILSKHPNWTNTQVRS

SLENTTTKLGDSFYYGKGLINVQAAAQ

AmyE protein sequence
SEQ ID NO: 7
LTAPSIKSGTILHAWNWSFNTLKHNMKDIHDAGYTAIQTSPINQVKEGNQGDKSMSNWYWLY

QPTSYQIGNRYLGTEQEFKEMCAAAEEYGIKVIVDAVINHTTSDYAAISNEVKSIPNWTHGN

TQIKNWSDRWDVTQNSLLGLYDWNTQNTQVQSYLKRFLDRALNDGADGFRFDAAKHIELPDD

GSYGSQFWPNITNTSAEFQYGEILQDSASRDAAYANYMDVTASNYGHSIRSALKNRNLGVSN

ISHYASDVSADKLVTWVESHDTYANDDEESTWMSDDDIRLGWAVIASRSGSTPLFFSRPEGG

GNGVRFPGKSQIGDRGSALFEDQAITAVNRFHNVMAGQPEELSNPNGNNQIFMNQRGSHGVV

LANAGSSSVSINTATKLPDGRYDNKAGAGSFQVNDGKLTGTINARSVAVLYPD

Pectate Lyase C protein sequence
SEQ ID NO: 8
MKKIVSILFMFGLVMGFSQFQPSTVFAADKVVHETIIVPKNTTYDGKGQRFVAGKELGDSQ

SENQDPVFRVEDGATLKNVVLGAPAADGVHTYGNVNIQNVKWEDVGEDALTVKKEGKVTIDG

GSAQKASDKIFQINKASTFTVKNFTADNGGKFIRQLGGSTFHVDVIIDKCTITNMKEAIFRT

DSKTSTVRMTNTRYSNVGQKWIGVQHIYENNNTQF

---

The invention claimed is:

1. A method for increasing expression of a protein of interest (POI) in a *Bacillus* spp. bacterial cell comprising:
    (a) obtaining an altered *Bacillus* cell producing a protein of interest, wherein the altered *Bacillus* cell comprises a genetic alteration of the sinR gene comprising a G to A silent mutation at a nucleotide position corresponding to nucleotide position 330 of SEQ ID NO: 1; and
    (b) culturing the altered *Bacillus* cell under conditions such that the POI is expressed, wherein the increased amount of the POI is relative to the expression of the same POI in an unaltered *Bacillus* spp. cell.

2. The method of claim 1, wherein the *Bacillus* cell is selected from the group consisting of *B. subtilis, B. licheniformis, B. lentus, B. brevis, B. stearothermophilus, B. alkalophilus, B. amyloliquefaciens, B. clausii, B. sonorensis, B. halodurans, B. pumilus, B. lautus, B. pabuli, B. cereus, B. agaradhaerens, B akibai, B. clarkii, B. pseudofirmus, B. lehensis, B. megaterium, B. coagulans, B. circulans, B. gibsonii,* and *B. thuringiensis.*

3. The method of claim 1, wherein the POI is encoded by a gene heterologous to the altered bacterial cell or a gene endogenous to the altered bacterial cell.

4. The method of claim 1, wherein the POI is an enzyme is selected from the group consisting of acetyl esterases, aminopeptidases, amylases, arabinases, arabinofuranosidases, carboxypeptidases, catalases, cellulases, chitinases, chymosin, cutinase, deoxyribonucleases, epimerases, esterases, α-galactosidases, β-galactosidases, α-glucanases, glucan lysases, endo-β-glucanases, glucoamylases, glucose oxidases, α-glucosidases, β-glucosidases, glucuronidases, hemicellulases, hexose oxidases, hydrolases, invertases, isomerases, laccases, lipases, lyases, mannosidases, oxidases, oxidoreductases, pectate lyases, pectin acetyl esterases, pectin depolymerases, pectin methyl esterases, pectinolytic enzymes, perhydrolases, polyol oxidases, peroxidases, phenoloxidases, phytases, polygalacturonases, proteases, rhamno-galacturonases, ribonucleases, transferases, transport proteins, transglutaminases, xylanases, hexose oxidases, and combinations thereof.

5. The method of claim 1, further comprising recovering the POI.

6. The method of claim 1, wherein the increased amount of an expressed POI relative to unaltered *Bacillus* spp. cell is at least 10%.

7. An altered *Bacillus* spp. bacterial cell expressing an increased amount of a protein of interest (POI) relative to the expression of the same POI in an unaltered *Bacillus* spp. cell, wherein the altered cell comprises a genetic alteration of the sinR gene comprising a G to A silent mutation at a nucleotide position corresponding to nucleotide position 330 of SEQ ID NO: 1.

8. The altered cell of claim 7, wherein the *Bacillus* cell is selected from the group consisting of *B. subtilis, B. licheniformis, B. lentus, B. brevis, B. stearothermophilus, B. alkalophilus, B. amyloliquefaciens, B. clausii, B. sonorensis, B. halodurans, B. pumilus, B. lautus, B. pabuli, B. cereus, B. agaradhaerens, B akibai, B. clarkii, B. pseudofirmus, B. lehensis, B. megaterium, B. coagulans, B. circulans, B. gibsonii*, and *B. thuringiensis*.

9. The altered cell of claim 7, wherein the POI is encoded by a gene heterologous to the altered bacterial cell or a gene endogenous to the altered bacterial cell.

10. The altered cell of claim 7, wherein the POI is an enzyme is selected from the group consisting of acetyl esterases, aminopeptidases, amylases, arabinases, arabinofuranosidases, carboxypeptidases, catalases, cellulases, chitinases, chymosin, cutinase, deoxyribonucleases, epimerases, esterases, α-galactosidases, β-galactosidases, α-glucanases, glucan lysases, endo-β-glucanases, glucoamylases, glucose oxidases, α-glucosidases, β-glucosidases, glucuronidases, hemicellulases, hexose oxidases, hydrolases, invertases, isomerases, laccases, lipases, lyases, mannosidases, oxidases, oxidoreductases, pectate lyases, pectin acetyl esterases, pectin depolymerases, pectin methyl esterases, pectinolytic enzymes, perhydrolases, polyol oxidases, peroxidases, phenoloxidases, phytases, polygalacturonases, proteases, rhamno-galacturonases, ribonucleases, thaumatin, transferases, transport proteins, transglutaminases, xylanases, hexose oxidases, and combinations thereof.

11. The altered cell of claim 7, wherein the increased amount of an expressed POI relative to the unaltered *Bacillus* spp. cell is at least 10%.

12. A polynucleotide comprising a G to A silent mutation at a nucleotide position corresponding to nucleotide position 330 of SEQ ID NO: 1.

13. A vector comprising the polynucleotide sequence of claim 12.

* * * * *

SEQUENCE LISTING

<160> NUMBER OF SEQ IDS NOS: 8

<210> SEQ ID NO 1
<211> LENGTH: 336
<212> TYPE: DNA
<213> ORGANISM: Unknown
<220> FEATURE:
<223> OTHER INFORMATION: Bacillus sp.

<400> SEQUENCE: 1
ttgattggcc agcgtattaa acaataccgt aaagaaaaag gctactcact atcagaacta     60
gctgaaaaag ctggggtagc gaagtcttat ttaagctcaa tagaacgaaa tctacaaacg    120 aaccccctcca ttcaatttct cgaaaaagtc tccgctgttc tggacgtctc ggttcatact   180
ttgctcgatg agaaacatga aaccgaatac gatggtcaat tagatagtga atgggagaaa    240

```
ttggttcgcg atgcgatgac atccggggta tcgaaaaaac aatttcgtga attttagat      300 tatcaaaaat ggagaaaatc ccaaaaagag gagtag                              336
```

<210> SEQ ID NO 2
<211> LENGTH: 111
<212> TYPE: PRT
<213> ORGANISM: Unknown
<220> FEATURE:
<223> OTHER INFORMATION: Bacillus sp.

<400> SEQUENCE: 2

```
Met Ile Gly Gln Arg Ile Lys Gln Tyr Arg Lys Glu Lys Gly Tyr Ser
1               5                   10                  15

Leu Ser Glu Leu Ala Glu Lys Ala Gly Val Ala Lys Ser Tyr Leu Ser
            20                  25                  30

Ser Ile Glu Arg Asn Leu Gln Thr Asn Pro Ser Ile Gln Phe Leu Glu
        35                  40                  45

Lys Val Ser Ala Val Leu Asp Val Ser Val His Thr Leu Leu Asp Glu
    50                  55                  60

Lys His Glu Thr Glu Tyr Asp Gly Gln Leu Asp Ser Glu Trp Glu Lys
65                  70                  75                  80

Leu Val Arg Asp Ala Met Thr Ser Gly Val Ser Lys Lys Gln Phe Arg
                85                  90                  95

Glu Phe Leu Asp Tyr Gln Lys Trp Arg Lys Ser Gln Lys Glu Glu
            100                 105                 110
```

<210> SEQ ID NO 3
<211> LENGTH: 336
<212> TYPE: DNA
<213> ORGANISM: Artificial Sequence
<220> FEATURE:
<223> OTHER INFORMATION: synthetic construct

<400> SEQUENCE: 3

```
ttgattggcc agcgtattaa acaataccgt aaagaaaaag gctactcact atcagaacta     60
gctgaaaaag ctggggtagc gaagtcttat ttaagctcaa tagaacgaaa tctacaaacg    120 aaccccctcca ttcaatttct cgaaaaagtc tccgctgttc tggacgtctc ggttcatact   180
ttgctcgatg agaaacatga aaccgaatac gatggtcaat tagatagtga atgggagaaa    240
ttggttcgcg atgcgatgac atccggggta tcgaaaaaac aatttcgtga attttagat    300 tatcaaaaat ggagaaaatc ccaaaaagaa gagtag                              336
```

<210> SEQ ID NO 4
<211> LENGTH: 35
<212> TYPE: DNA
<213> ORGANISM: Artificial Sequence
<220> FEATURE:
<223> OTHER INFORMATION: Forward Primer

<400> SEQUENCE: 4

```
caggaattcc tgacgtctca aatatgtgac tattg                               35
```

<210> SEQ ID NO 5
<211> LENGTH: 34
<212> TYPE: DNA
<213> ORGANISM: Artificial Sequence
<220> FEATURE:
<223> OTHER INFORMATION: Reverse Primer

<400> SEQUENCE: 5
ctcggatccg agaaattgaa agaaagacaa aagc         34

<210> SEQ ID NO 6
<211> LENGTH: 275
<212> TYPE: PRT
<213> ORGANISM: Unknown
<220> FEATURE:
<223> OTHER INFORMATION: Bacillus sp.

<400> SEQUENCE: 6

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
    50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
        115                 120                 125

Pro Ser Gly Ser Ala Ala Leu Lys Ala Ala Val Asp Lys Ala Val Ala
    130                 135                 140

Ser Gly Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Leu Asn Gly Thr Ser Met Ala Ser
    210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275

<210> SEQ ID NO 7
<211> LENGTH: 425
<212> TYPE: PRT
<213> ORGANISM: Unknown
<220> FEATURE:
<223> OTHER INFORMATION: Bacillus sp.

<400> SEQUENCE: 7

Leu Thr Ala Pro Ser Ile Lys Ser Gly Thr Ile Leu His Ala Trp Asn
1               5                   10                  15

```
Trp Ser Phe Asn Thr Leu Lys His Asn Met Lys Asp Ile His Asp Ala
             20                  25                  30

Gly Tyr Thr Ala Ile Gln Thr Ser Pro Ile Asn Gln Val Lys Glu Gly
         35                  40                  45

Asn Gln Gly Asp Lys Ser Met Ser Asn Trp Tyr Trp Leu Tyr Gln Pro
     50                  55                  60

Thr Ser Tyr Gln Ile Gly Asn Arg Tyr Leu Gly Thr Glu Gln Glu Phe
 65                  70                  75                  80

Lys Glu Met Cys Ala Ala Ala Glu Glu Tyr Gly Ile Lys Val Ile Val
                 85                  90                  95

Asp Ala Val Ile Asn His Thr Thr Ser Asp Tyr Ala Ala Ile Ser Asn
             100                 105                 110

Glu Val Lys Ser Ile Pro Asn Trp Thr His Gly Asn Thr Gln Ile Lys
         115                 120                 125

Asn Trp Ser Asp Arg Trp Asp Val Thr Gln Asn Ser Leu Leu Gly Leu
     130                 135                 140

Tyr Asp Trp Asn Thr Gln Asn Thr Gln Val Gln Ser Tyr Leu Lys Arg
145                 150                 155                 160

Phe Leu Asp Arg Ala Leu Asn Asp Gly Ala Asp Gly Phe Arg Phe Asp
                 165                 170                 175

Ala Ala Lys His Ile Glu Leu Pro Asp Asp Gly Ser Tyr Gly Ser Gln
             180                 185                 190

Phe Trp Pro Asn Ile Thr Asn Thr Ser Ala Glu Phe Gln Tyr Gly Glu
         195                 200                 205

Ile Leu Gln Asp Ser Ala Ser Arg Asp Ala Ala Tyr Ala Asn Tyr Met
    210                 215                 220

Asp Val Thr Ala Ser Asn Tyr Gly His Ser Ile Arg Ser Ala Leu Lys
225                 230                 235                 240

Asn Arg Asn Leu Gly Val Ser Asn Ile Ser His Tyr Ala Ser Asp Val
                 245                 250                 255

Ser Ala Asp Lys Leu Val Thr Trp Val Glu Ser His Asp Thr Tyr Ala
             260                 265                 270

Asn Asp Asp Glu Glu Ser Thr Trp Met Ser Asp Asp Asp Ile Arg Leu
         275                 280                 285

Gly Trp Ala Val Ile Ala Ser Arg Ser Gly Ser Thr Pro Leu Phe Phe
    290                 295                 300

Ser Arg Pro Glu Gly Gly Gly Asn Gly Val Arg Phe Pro Gly Lys Ser
305                 310                 315                 320

Gln Ile Gly Asp Arg Gly Ser Ala Leu Phe Glu Asp Gln Ala Ile Thr
                 325                 330                 335

Ala Val Asn Arg Phe His Asn Val Met Ala Gly Gln Pro Glu Glu Leu
             340                 345                 350

Ser Asn Pro Asn Gly Asn Asn Gln Ile Phe Met Asn Gln Arg Gly Ser
         355                 360                 365

His Gly Val Val Leu Ala Asn Ala Gly Ser Ser Val Ser Ile Asn
    370                 375                 380

Thr Ala Thr Lys Leu Pro Asp Gly Arg Tyr Asp Asn Lys Ala Gly Ala
385                 390                 395                 400

Gly Ser Phe Gln Val Asn Asp Gly Lys Leu Thr Gly Thr Ile Asn Ala
                 405                 410                 415

Arg Ser Val Ala Val Leu Tyr Pro Asp
             420                 425
```

```
-continued

<210> SEQ ID NO 8
<211> LENGTH: 221
<212> TYPE: PRT
<213> ORGANISM: Unknown
<220> FEATURE:
<223> OTHER INFORMATION: Bacillus sp.

<400> SEQUENCE: 8

Met Lys Lys Ile Val Ser Ile Leu Phe Met Phe Gly Leu Val Met Gly
1               5                   10                  15

Phe Ser Gln Phe Gln Pro Ser Thr Val Phe Ala Ala Asp Lys Val Val
            20                  25                  30

His Glu Thr Ile Ile Val Pro Lys Asn Thr Thr Tyr Asp Gly Lys Gly
        35                  40                  45

Gln Arg Phe Val Ala Gly Lys Glu Leu Gly Asp Gly Ser Gln Ser Glu
    50                  55                  60

Asn Gln Asp Pro Val Phe Arg Val Glu Asp Gly Ala Thr Leu Lys Asn
65                  70                  75                  80

Val Val Leu Gly Ala Pro Ala Ala Asp Gly Val His Thr Tyr Gly Asn
                85                  90                  95

Val Asn Ile Gln Asn Val Lys Trp Glu Asp Val Gly Glu Asp Ala Leu
            100                 105                 110

Thr Val Lys Lys Glu Gly Lys Val Thr Ile Asp Gly Gly Ser Ala Gln
        115                 120                 125

Lys Ala Ser Asp Lys Ile Phe Gln Ile Asn Lys Ala Ser Thr Phe Thr
    130                 135                 140

Val Lys Asn Phe Thr Ala Asp Asn Gly Gly Lys Phe Ile Arg Gln Leu
145                 150                 155                 160

Gly Gly Ser Thr Phe His Val Asp Val Ile Ile Asp Lys Cys Thr Ile
                165                 170                 175

Thr Asn Met Lys Glu Ala Ile Phe Arg Thr Asp Ser Lys Thr Ser Thr
            180                 185                 190

Val Arg Met Thr Asn Thr Arg Tyr Ser Asn Val Gly Gln Lys Trp Ile
        195                 200                 205

Gly Val Gln His Ile Tyr Glu Asn Asn Asn Thr Gln Phe
    210                 215                 220
```